United States Patent
Tokunaga et al.

(10) Patent No.: US 6,743,588 B2
(45) Date of Patent: Jun. 1, 2004

(54) FLUORESCENT DYE AND METHOD OF MEASURING NUCLEIC ACID

(75) Inventors: Takumi Tokunaga, Kanagawa (JP); Takahiko Ishiguro, Kanagawa (JP); Ryuichi Horie, Kanagawa (JP)

(73) Assignee: Tosoh Corporation, Shinnanyo (JP)

( * ) Notice: Subject to any disclaimer, the term of this patent is extended or adjusted under 35 U.S.C. 154(b) by 2 days.

(21) Appl. No.: 10/042,193

(22) Filed: Jan. 11, 2002

(65) Prior Publication Data

US 2002/0192670 A1 Dec. 19, 2002

(30) Foreign Application Priority Data

Jan. 11, 2001 (JP) ............................. 2001-003432

(51) Int. Cl.[7] .................. C12Q 1/68; C12P 19/34; C07H 21/00; C07H 21/02; C09B 67/00

(52) U.S. Cl. .................. 435/6; 435/91.1; 435/91.2; 8/636; 8/648; 536/24.3; 536/26.6

(58) Field of Search ................ 435/6, 91.1, 91.2; 8/638, 648; 536/24.3, 26.6

*Primary Examiner*—Jezia Riley
(74) *Attorney, Agent, or Firm*—Oblon, Spivak, McClelland, Maier & Neustadt, P.C.

(57) ABSTRACT

A compound represented by the formula 1, a salt, hydrate, solvate or stereoisomer thereof.

Formula 1

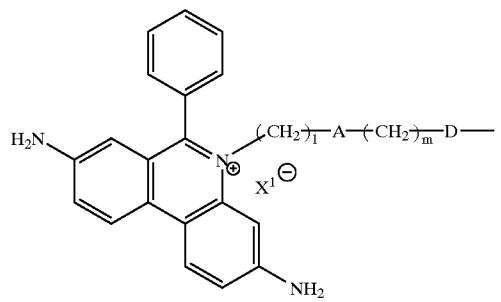

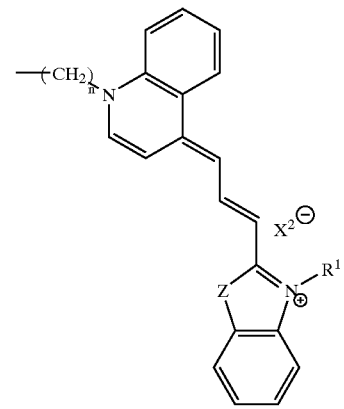

21 Claims, 4 Drawing Sheets

SEQUENCE LISTING

<160> NUMBER OF SEQ ID NOS: 4

<210> SEQ ID NO 1
<211> LENGTH: 30
<212> TYPE: DNA
<213> ORGANISM: ARTIFICIAL SEQUENCE
<220> FEATURE:
<223> OTHER INFORMATION: SYNTHETIC DNA

<400> SEQUENCE: 1 ttttttttt tttttttttt tttttttttt        30

<210> SEQ ID NO 2
<211> LENGTH: 30
<212> TYPE: DNA
<213> ORGANISM: ARTIFICIAL SEQUENCE
<220> FEATURE:
<223> OTHER INFORMATION: SYNTHETIC DNA

<400> SEQUENCE: 2
aaaaaaaaaa aaaaaaaaaa aaaaaaaaaa        30

<210> SEQ ID NO 3
<211> LENGTH: 20
<212> TYPE: DNA
<213> ORGANISM: ARTIFICIAL SEQUENCE
<220> FEATURE:
<223> OTHER INFORMATION: SYNTHETIC DNA

<400> SEQUENCE: 3
tgtttgaggg tggatagcag        20

<210> SEQ ID NO 4
<211> LENGTH: 20
<212> TYPE: DNA
<213> ORGANISM: ARTIFICIAL SEQUENCE
<220> FEATURE:
<223> OTHER INFORMATION: SYNTHETIC DNA

<400> SEQUENCE: 4
ctgctatcca ccctcaaaca        20

FLUORESCENT DYE AND METHOD OF MEASURING NUCLEIC ACID

The present invention relates to a novel fluorescent dye, a method of its production, a nucleic acid probe linked to the dye by a chemical bond and a method of measuring a nucleic acid using the probe. In particular, the present invention relates to a novel fluorescent dye which shows a large Stokes shift and enhance its fluorescence intensity in the presence of a double-stranded nucleic acid, a method of producing it, a nucleic acid probe obtained by chemically linking the dye, and a method of measuring a nucleic acid characterized by the use of it.

The method of the present invention relates to a method of qualitative or quantitative assay of a target RNA containing a specific base sequence anticipated in a gene mixture such as DNA and RNA. The method of the present invention is useful in gene diagnosis and other areas of clinical diagnostics and in identification or quantification of microorganisms in food and in the environment such as in rooms, soil, rivers and sea.

Generally, assays of biogenic components require high specificity and sensitivity. Assays of a specific nucleic acid having a specific base sequence (target nucleic acid) utilizes sequence-specific hybridizability of the nucleic acid with a complementary nucleic acid (a nucleic acid probe).

Generation of a measurable signal corresponding to the amount to the hybridization product is essential for quantification of a target nucleic acid having a specific base sequence. In quantification of a target nucleic acid for clinical diagnosis, because samples may contain the target nucleic acid only in trace amounts, the signal generation has to involve amplification of a trace amount of the nucleic acid.

Especially, in diagnosis of virus infections, for sensitive and reproducible assay of the target nucleic acid (viral nucleic acid) which is usually found in trace amounts in clinical samples, preamplification of the target nucleic acid by polymerase chain reaction (PCR) has been proposed to increase the sensitivity through signal enhancement. For RNA amplification, techniques called NASBA (Patent No. 2650159) and 3SR (EP-A-373960) are known.

A nucleic acid probe having a nucleic acid sequence complementary to a specific base sequence in a target nucleic acid, which is so labeled with a fluorescent intercalative dye as to give off a measurable fluorescent signal upon binding to the target nucleic acid (Japanese Unexamined Patent Publication JP-A-8-211050) gives off a measurable fluorescent signal upon hybridization with the target acid. The probe makes it possible to detect hybridization and quantify the hybridization product without the need to separate the unhybridized probe from the reaction system and has the advantage that it does not give false positive results attributable to carryover of the amplification product because sampling from reaction vessels is no longer needed after amplification.

Further, support-free isothermal assay of a target RNA in a closed system during amplification of the target RNA which is characterized in that isothermal amplification of an RNA having a specific nucleotide sequence by the action of nucleic acid primers and nucleic acid polymerases is carried out in the presence of the nucleic acid probe, has been developed (Japanese Patent Application JP12-144000).

Intercalative fluorescent dyes intercalate into double-stranded nucleic acids and changes their fluorescence characteristics as they lose freedom upon intercalation. As compound having such characteristics, ethidium bromide, oxazole yellow, thiazol orange and the like are known. Further, dimers of these compounds obtained by linking their molecules via a linker such as ethidium diner, YOYO and the like are also known to show fluorescent enhancement upon intercalation into double-stranded nucleic acids. Therefore, if two or more fluorescent intercalative dyes which change their fluorescent characteristics distinguishably are so used as to enable simultaneous measurement of multiple nucleic acids during their amplification, there are numerous possible applications of industrial significance. For example, it is possible to detect multiple target nucleic acids simultaneously, or check if a target nucleic acid is being amplified successfully or quantify a target acid by amplifying a known amount of a standard nucleic acid together with the target nucleic acid.

However, the number of intercalative dyes is not infinite, and the spectra of the fluorescent radiations from them have maximum values at certain wavelengths from which they spread to both sides, and their fluorescent quantum yields are generally different. Therefore, with fluorescent intercalative dyes having overlapping spectra, precise fluorescence measurement at a certain wavelength is difficult. Besides, because the types of lasers and light emitting diodes available as radiation sources to excite florescent intercalative dyes are limited, it has been very tough to select two or more fluorescent intercalative dyes that do not overlapping fluorescent spectra in view of optimum combination of sources of excitation radiations. For example, although cyanine dyes such as oxazole yellow and thiazole orange are known as fluorescent intercalative dyes, the difference between the maximum fluorescence wavelengths of two cyanine dyes has to be at least about 100 nm in order to avoid a spectral overlap between them. However, the difference between the maximum emission wavelength and the maximum excitation wavelength of a cyanine fluorescent substance is only from 20 to 40 nm. However, because fluorometric excitation of two dyes requires two radiation sources, the need for two radiation sources restricts the fluorometric use of these dyes.

The first object of the present invention is to provide a compound as a novel fluorescent intercalative dye which shows a large fluorescent enhancement upon intercalation into a double-stranded nucleic acid when used in detection of the nucleic acid, shows a great difference between the excitation wavelength and the emission wavelength (i.e., has a large Stokes shift) and does not have a fluorescent spectrum that overlaps with those of conventionally known fluorescent intercalative dyes. The second object of the present invention is to provide a novel nucleic acid probe having the fluorescent dye chemically linked. The third object of the present invention is to provides a method of measuring (identifying or quantifying) a nucleic acid using the nucleic acid probe which comprises amplifying at least one target nucleic acid and measuring the amplification product in a closed vessel without any separation operation to detect and quantify the target nucleic acid with great precision, especially a method of measuring at least two target nucleic acids simultaneously.

It is widely known that when one of two neighboring compounds which meet specific conditions is excited, the energy transfers to the other and is emitted as fluorescence from the compound which receives the energy (the energy acceptor). The present inventors conducted extensive research on substances which efficiently transfer energy in the molecule and found out a novel fluorescent dye which shows a large enhancement in fluorescent intensity upon intercalation into a double stranded nucleic acid in the detection of a nucleic acid and shows a large difference between its excitation wavelength and emission wavelength (i.e. a large Stokes shift). Thus, the present invention is accomplished to attain the above-mentioned objects. According to a first aspect of the invention, the present invention provides a novel compound represented by the formula 1, or a salt, hydrate, solvate or stereoisomer thereof whose structure, synthesis or fluorescent characteristics have not been known (wherein $R^1$ is a lower alkyl group, each of A and D, which may be the same or different, is a group represented by the formula $CHR^2$ —(wherein $R^2$ is a hydrogen atom, a lower alkyl group or a lower alkyl group substituted with a halogen atom), a group represented by the formula —$NR^3$—(wherein $R^3$ is a hydrogen atom, a lower alkyl group or a lower alkyl group substituted with a halogen atom), a group represented by the formula —$N^+R^4R^5 \cdot Q^-$- (wherein each of $R^4$ and $R^5$, which may be the same or different, is a lower alkyl group or a lower alkyl group substituted with a halogen atom, and Q is a halogen atom, a group represented by the formula $R^6COO$ (wherein $R^6$ is a lower alkyl group or a lower alkyl group substituted with a halogen atom) or a group represented by the formula $R^7SO_3$ (wherein $R^7$ is a lower alkyl group, a lower alkyl group substituted with a halogen atom or a phenyl group which may be substituted with a lower alkyl group)), an oxygen atom or a sulfur atom, each of l, m and n, which may be the same or different, is an integer of from 2 to 5, Z is an oxygen atom or a sulfur atom, and each of $X^1$ and $X^2$, which may be the same or different, is a halogen atom, a group represented by the formula $R^8COO$ (wherein $R^8$ is a lower alkyl group or a lower alkyl group substituted with a halogen atom) or a group represented by the formula $R^9SO_3$ (wherein $R^9$ is a lower alkyl group, a lower alkyl group substituted with a halogen atom or a phenyl group which may be substituted with a lower alkyl group)) whose structure, synthesis or fluorescent characteristics have not been known.

According to a second aspect, the present invention provides a method of producing the compound as defined in the first aspect, a salt, hydrate, solvate or stereoisomer thereof.

3. A method of detecting or quantifying a nucleic acid anticipated to be contained in a sample, which uses the compound as defined in the first aspect.

According to a third aspect, the present invention provides a method of producing the compound as defined in the first aspect, a salt, hydrate, solvate or stereoisomer thereof. According to a fourth aspect, the present invention provides the method according to the third aspect, wherein the nucleic acid is a double-stranded DNA, a double-stranded RNA or a DNA-RNA hybrid or a combination of them.

According to a fifth aspect, the present invention provides a nucleic acid probe comprising a single-stranded oligonucleotide having a sequence complementary to a specific sequence in a nucleic acid (target nucleic acid) containing the specific sequence and a compound represented by formula 1 liked to the single-stranded oligonucleotide by a chemical bond. According to a sixth aspect, the present invention provides the nucleic acid probe according to the fifth aspect, wherein the single-stranded oligonucleotide is a DNA oligomer. According to a seventh aspect, the present invention provides the nucleic acid probe according to the sixth aspect, wherein a phosphorus atom in the DNA oligomer is linked by the chemical bond via a linker. According to an eighth aspect, the present invention provides the nucleic acid probe according to the seventh aspect, wherein the compound represented by the formula 1 alters its fluorescent characteristics upon intercalation into the double strand resulting from hybridization of the target nucleic acid and the single-stranded DNA probe.

According to a ninth aspect, the present invention provides a method of measuring at least one nucleic acid (target nucleic acid) containing a specific nucleic acid sequence in a sample, which uses the nucleic acid probe as defined in the sixth aspect.

According to a tenth aspect, the present invention provides a method of measuring at least two RNAs (target RNAs) having specific nucleic acid sequences in a sample, which comprises a step of amplifying the target RNAs simultaneously in the presence of probes which are complementary to the respective amplification products and labeled with different fluorescent intercalative dyes, and a step of measuring the change in fluorescence intensity resulting from intercalation into the double strands formed by hybridization of the amplification products and the probes, wherein one of the fluorescent intercalative dyes is the compound represented by the formula 1, and the other is a fluorescent intercalative dye which is excited by a radiation at the same wavelength as the compound represented by the formula 1 but emits fluorescence at a wavelength different from the wavelength of the fluorescence from the compound represented by the formula 1. According to an eleventh aspect, the present invention provides a method of measuring at least one RNA (target RNA) having a specific nucleic acid sequence in a sample, which comprises a step of amplifying the target RNA and a known amount of a standard nucleic acid added to the sample simultaneously in the presence of probes which are complementary to the respective amplification products and labeled with different fluorescent intercalative dyes, a step of measuring the fluorescence intensity which has changed due to intercalation of the fluorescent intercalative dyes into the double strands formed by hybridization of the amplification products and the probes, and comparing the fluorescence intensity with that measured in the presence of a known amount of the standard nucleic acid, wherein one of the fluorescent intercalative dyes is the compound represented by the formula 1, and the other is a fluorescent intercalative dye which is excited by a radiation at the same wavelength as the compound represented by the formula 1 but emits fluorescence at a wavelength different from the wavelength of the fluorescence from the compound represented by the formula 1.

According to a twelfth aspect, the present invention provides the method according to the tenth or eleventh aspects, wherein the other fluorescent intercalative dye is oxazole yellow. According to a thirteenth aspect, the present invention provides the method according to the twelfth aspect, the excitation wavelengths of the fluorescent intercalative dyes are from 450 nm to 500 nm. Now, the present invention will be described in detail. Herein, the term "lower" means a linear or branched chain of from 1 to 6 atoms unless otherwise noted.

FIG. 1 shows the fluorescent spectra of compound 1 obtained in Example 5 (1) in the absence of a double-stranded nucleic acid at an excitation wavelength of 488 nm, (2) in the presence of dT30mer (0.04 mmol) and dA30mer (0.04 mmol) at an excitation wavelength of 470 nm, and (3) in the presence of dT30mer (0.04 mmol) and dA30mer (0.04 mmol) at an excitation wavelength of 488 nm.

FIG. 2 shows the fluorescent spectra of compound 2 obtained in Example 6 (1) in the absence of a double-stranded nucleic acid at an excitation wavelength of 488 nm, (2) in the presence of dT30mer (0.04 mmol) and dA30mer (0.04 mmol) at an excitation wavelength of 470 nm, and (3) in the presence of dT30mer (0.04 mmol) and dA30mer (0.04 mmol) at an excitation wavelength of 488 nm.

In the formula 1, as a lower alkyl group, a methyl group, an ethyl group, a propyl group, an isopropyl group, a butyl group, an isobutyl group, a sec-butyl group, a tert-butyl group, a pentyl (or amyl) group, an isopentyl group, a neopentyl group, a tert-pentyl group, a 1-methylbutyl group, a 2-methylbutyl group, a 1,2-dimethylbutyl group, a hexyl group, an isohexyl group or a 3-methylpentyl group may specifically mentioned. Preferred is a methyl group, an ethyl group, a propyl group, an isopropyl group, a butyl group, a pentyl (or amyl) group or a hexyl group. In the formula 1, as a lower alkyl group substituted with a halogen atom, a fluoromethyl group, a difluoromethyl group, a trifluoromethyl group, a 3-fluoropropyl group, a chloromethyl group, a dichloromethyl group, a trichloromethyl group, a 3-chloroproply group, a 4-chlorobutyl group, a 5-chloropentyl group, a 6-chlorohexyl group, a 3-bromopropyl group, a 4-bromobutyl group, a 5-bromopentyl group, a 6-bromohexyl group, a 3-iodopropyl group, a 4-iodobutyl group, a 5-iodopentyl group or a 6-iodohexyl group may, for example, be mentioned. As a halogen atom in the formula 1, a fluorine atom, a chlorine atom, a bromine atom or an iodine atom may be mentioned.

To definitely explain the compounds (aromatic compound derivatives, their salts, hydrates, solvates and stereoisomers) of the present invention represented by the formula 1, preferable specific examples of various symbols used in the formula 1 are described below in detail.

R is a lower alkyl group, preferably a linear or branched $C_{1-4}$ alkyl group such as a methyl group, an ethyl group or a propyl group, particularly preferably a methyl group or an ethyl group. A methyl group is the most preferable alkyl group as R above all.

A and D may be the same or different and each represents a group represented by the formula —$CHR^2$— (wherein $R^2$ is a hydrogen atom, a lower alkyl group or a lower alkyl group substituted with a halogen atom), a group represented by the formula —$NR^3$— (wherein $R^3$ is a hydrogen atom, a lower alkyl group or a lower alkyl group substituted with a halogen atom), a group represented by the formula —$N^+R^4R^5 \cdot Q^-$— (wherein each of $R^4$ and $R^5$, which may be the same or different, is a lower alkyl group or a lower alkyl group substituted with a halogen atom, and Q is a halogen atom, a group represented by the formula $R^6COO$ (wherein $R^6$ is a lower alkyl group or a lower alkyl group substituted with a halogen atom) or a group represented by the formula $R^7SO_3$ (wherein $R^7$ is a lower alkyl group, a lower alkyl group substituted with a halogen atom or a phenyl group which may be substituted with a lower alkyl group)), an oxygen atom or a sulfur atom. Preferably, A and D may be the same or different and each represents a group represented by the formula —$NR^3$— (wherein $R^3$ is a hydrogen atom, a lower alkyl group or a lower alkyl group substituted with a halogen atom), a group represented by the formula —$N^+R^4R^5 \cdot Q^-$—(wherein each of $R^4$ and $R^5$, which may be the same or different, is a lower alkyl group or a lower alkyl group substituted with a halogen atom, and Q is a halogen atom, a group represented by the formula $R^6COO$ (wherein $R^6$ is a lower alkyl group or a lower alkyl group substituted with a halogen atom) or a group represented by the formula $R^7SO_3$ (wherein $R^7$ is a lower alkyl group, a lower alkyl group substituted with a halogen atom or a phenyl group which may be substituted with a lower alkyl group)) or an oxygen atom. More preferably, A and D may be the same or different and each represents a group represented by the formula —$NR^3$— (wherein $R^3$ is a hydrogen atom, a lower alkyl group or a lower alkyl group substituted with a halogen atom) or a group represented by the formula —$N^+R^4R^5.Q^-$—(wherein each of $R^4$ and $R^5$, which may be the same or different, is a lower alkyl group or a lower alkyl group substituted with a halogen atom, and Q is a halogen atom, a group represented by the formula $R^6COO$ (wherein $R^6$ is a lower alkyl group or a lower alkyl group substituted with a halogen atom) or a group represented by the formula $R^7SO_3$ (wherein R is a lower alkyl group, a lower alkyl group substituted with a halogen atom or a phenyl group which may be substituted with a lower alkyl group)).

Q is a halogen atom, a group represented by the formula $R^6COO$ (wherein $R^6$ is a lower alkyl group or a lower alkyl group substituted with a halogen atom) or a group represented by the formula $R^7SO_3$ (wherein $R^7$ is a lower alkyl group, a lower alkyl group substituted with a halogen atom or a phenyl group which may be substituted with a lower alkyl group), preferably a halogen atom or a group represented by the formula $R^7SO_3$ (wherein $R^7$ is a lower alkyl group, a lower alkyl group substituted with a halogen atom or a phenyl group which may be substituted with a lower alkyl group), most preferably a halogen atom. 1, m and n are the same or different integers of from 2 to 5, preferably the same or different integers of from 2 to 4, particularly preferably the same or different integers of 2 or 3.

$R^2$ is a hydrogen atom, a lower alkyl group or a lower alkyl group substituted with a halogen atom, preferably a hydrogen atom or a lower alkyl group, particularly preferably a hydrogen atom, a methyl group or an ethyl group. Among them, a hydrogen atom is most preferable.

$R^3$ is a hydrogen atom, a lower alkyl group or a lower alkyl group substituted with a halogen atom, preferably a hydrogen atom; a methyl group, an ethyl group, a propyl group or a lower alkyl group substituted with a halogen atom such as a 2-iodoethyl group, a 3-iodopropyl group, a 4-iodobutyl group, a 5-iodopentyl group, a 6-iodohexyl group, a 2-buromoethyl group, a 3-bromopropyl group, a 4-bromobutyl group, a 5-bromopentyl group, a 6-bromohexyl group, a 2-chloroethyl group, a 3-chloropropyl group, a 4-chlorobutyl group, a 5-chloropentyl group or a 6-chlorohexyl group. Particularly preferably, $R^3$ is a hydrogen atom; a methyl group, an ethyl group, a propyl group or a lower alkyl group substituted with an iodine atom such as a 2-iodoethyl group, a 3-iodopropyl group, a 4-iodobutyl group, a 5-iodopentyl group or a 6-idohexyl group. More particularly preferred is a hydrogen atom, a methyl group, an ethyl group; a 2-iodoethyl group, a 3-iodopropyl group, a 4-iodobutyl group, a 5-iodopenthyl group or a 6-iodohexyl group.

$R^4$ and $R^5$ may be the same or different, and each of them is a lower alkyl group or a lower alkyl group substituted with a halogen atom. Preferably, each of $R^4$ and $R^5$ is independently a methyl group, an ethyl group, a propyl group; a 2-iodoethyl group, a 3-iodopropyl group, a 4-iodobutyl group, a 5-iodobentyl group, a 6-iodohexyl group, a 2-bromoethyl group, a 3-bromoproply group, a 4-bromobutyl group, a 5-bromopenthyl group, a 6-bromohexyl group, a 2-chloroethyl group, a 3-chloropropyl group, a 4-chloropropyl group, a 5-chloropropyl group or a 6-chlorohexyl group. Particularly preferably, each of $R^4$ and $R^5$ is independently a methyl group, an ethyl group, a propyl group; a 2-iodoethyl group, a 3-iodopropyl group, a 4-iodobutyl group, a 5-iodobentyl group or a 6-iodohexyl group. More particularly preferably, each of $R^4$ and $R^5$ is independently a methyl group, an ethyl group; a 2-iodoethyl group, a 3-iodopropyl group, a 4-iodobutyl group, a 5-iodobentyl group or a 6-iodohexyl group.

$R^6$ is a lower alkyl group or a lower alkyl group substituted with a halogen atom, preferably a methyl group, an ethyl group, a propyl group; fluoromethyl group, a difluoromethyl group, a trifluoromethyl group, a chloromethyl group, a dichloromethyl group or a trichloromethyl group, particularly preferably a methyl group, a trifluoromethyl group or a trichloromethyl group.

$R^7$ is a lower alkyl group, a lower alkyl group substituted with a halogen atom or a phenyl group which may be substituted with a lower alkyl group preferably a methyl group, an ethyl group, a propyl group; a fluoromethyl group, a difluoromethyl group, a trifluoromethyl group, a chloromethyl group, a dichloromethyl group, a trichloromethyl group, a phenyl group or a p-methylphenyl group, particularly preferably a methyl group; a trifluoromethyl group, a trichloromethyl group; a phenyl group or a p-methylphenyl group.

Z is an oxygen atom or a sulfur atom, preferably a sulfur atom.

$X^1$ and $X^2$ may be the same or different, and each of them is a halogen atom, a group represented by the formula $R^8COO$ (wherein $R^8$ is a lower alkyl group or a lower alkyl group substituted with a halogen atom) or a group represented by the formula $R^9SO_3$ (wherein $R^9$ is a lower alkyl group, a lower alkyl group substituted with a halogen atom or a phenyl group which may be substituted with a lower alkyl group). Preferably, each of $X^1$ and $X^2$ is independently a halogen atom or a group represented by the formula $R^9SO_3$ (wherein $R^9$ is a lower alkyl group, a lower alkyl group substituted with a halogen atom or a phenyl group which may be substituted with a lower alkyl group). Particularly preferably, $X^1$ and $X^2$ are the same or different halogen atoms.

$R^8$ is a lower alkyl group or a lower alkyl group substituted with a halogen atom, preferably a methyl group, an ethyl group, a propyl group; a fluoromethyl group, a difluoromethyl group, a trifluoromethyl group, a chloromethyl group, a dichloromethyl group or a trifluoromethyl group, particularly preferably a methyl group, a trifluoromethyl group or a trichloromethyl group.

$R^9$ is a lower alkyl group, a lower alkyl group substituted with a halogen atom or a phenyl group which may be substituted with a lower alkyl group, preferably a methyl group, an ethyl group, a propyl group; a fluoromethyl group, a difluoromethyl group, a trifluoromethyl group, a chloromethyl group, a dichloromethyl group, a trichloromethyl group; a phenyl group or a p-methylphenyl group, particularly preferably a methyl group; a trifluoromethyl group, a trichloromethyl group; a phenyl group or a p-methylphenyl group.

Preferable examples of the compound of the present invention represented by the formula 1 are those wherein $R^1$ is a lower alkyl group, each of A and D, which may be the same or different, is a group represented by the formula —$CHR^2$— (wherein $R^2$ is a hydrogen atom or a lower alkyl group), a group represented by the formula —$NR^3$— (wherein $R^3$ is a hydrogen atom, a lower alkyl group or a lower alkyl group substituted with a halogen atom), a group represented by the formula —$N^+R^4R^5.Q^-$—(wherein each of $R^4$ and $R^5$, which may be the same or different, is a lower alkyl group or a lower alkyl group substituted with a halogen atom, and Q is a halogen atom or a group represented by the formula $R^7SO_3$ (wherein $R^7$ is a lower alkyl group, a lower alkyl group substituted with a halogen atom or a phenyl group which may be substituted with a lower alkyl group)), an oxygen atom or a sulfur atom, each of l, m and n, which may be the same or different, is an integer of from 2 to 5, Z is an oxygen atom or a sulfur atom, and each of $X^1$ and $X^2$, which may be the same or different, is a halogen atom or a group represented by the formula $R^9SO_3$ (wherein $R^9$ is a lower alkyl group, a lower alkyl group substituted with a halogen atom or a phenyl group which may be substituted with a lower alkyl group). Particularly preferred examples are those wherein $R^1$ is a lower alkyl group, each of A and D, which may be the same or different, is a group represented by the formula —$CHR^2$— (wherein $R^2$ is a hydrogen atom), a group represented by the formula —$NR^3$— (wherein $R^3$ is a hydrogen atom, a lower alkyl group or a lower alkyl group substituted with a halogen atom), a group represented by the formula —$N^+R^4R^5.Q^-$—(wherein each of $R^4$ and $R^5$, which may be the same or different, is a lower alkyl group or a lower alkyl group substituted with a halogen atom, and Q is a halogen atom or a group represented by the formula $R^7SO_3$ (wherein $R^7$ is a lower alkyl group, a lower alkyl group substituted with a halogen atom or a phenyl group which may be substituted with a lower alkyl group)) or an oxygen atom, each of l, m and n, which may be the same or different, is an integer of from 2 to 5, Z is an oxygen atom or a sulfur atom, and each of $X^1$ and $X^2$, which may be the same or different, is a halogen atom a group represented by the formula $R^9SO_3$ (wherein $R^9$ is a lower alkyl group, a lower alkyl group substituted with a halogen atom or a phenyl group which may be substituted with a lower alkyl group). Particularly preferred examples are those wherein $R^1$ is a lower alkyl group, each of A and D, which may be the same or different, is a group represented by the formula —$NR^3$— (wherein $R^3$ is a hydrogen atom, a lower alkyl group or a lower alkyl group substituted with a halogen atom) or a group represented by the formula —$N^+R^4R^5.Q^-$—(wherein each of $R^4$ and $R^5$, which may be the same or different, is a lower alkyl group or a lower alkyl group substituted with a halogen atom, and Q is a halogen atom or a group represented by the formula $R^7SO_3$ (wherein $R^7$ is a lower alkyl group, a lower alkyl group substituted with a halogen atom or a phenyl group which may be substituted with a lower alkyl group)), each of l, m and n, which may be the same or different, is an integer of from 2 to 4, Z is a sulfur atom, and each of $X^1$ and $X^2$, which may be the same or different, is a halogen atom or a group represented by the formula $R^9SO_3$ (wherein $R^9$ is a lower alkyl group, a lower alkyl group substituted with a halogen atom or a phenyl group which may be substituted with a lower alkyl group).

Among the above specific examples of the compound of the formula 1, those wherein $R^1$ is a methyl group or an ethyl group, each of A and D, which may be the same or different, is a group represented by the formula —$NR^3$— (wherein $R^3$ is a hydrogen atom; a methyl group, an ethyl group; a 2-iodoethyl group, a 3-iodopropyl group, a 4-iodobutyl group, a 5-iodopentyl group or a 6-iodohexyl group), or a group represented by the formula —$N^+R^4R^5.Q^-$—(wherein each of $R^4$ and $R^5$, which may be the same or different, is a methyl group, an ethyl group; a 2-iodoethyl group, a 3-iodopropyl group, a 4-iodobutyl group, a 5-iodopentyl group or a 6-iodohexyl group, and Q is a halogen atom or a or a group represented by the formula $R^7SO_3$ (wherein $R^7$ is a methyl group; a trifluoromethyl group, a trichloromethyl group; a phenyl group or a p-methylphenyl group)), each of l, m and n, which may be the same or different, is an integer of from 2 to 4, Z is a sulfur atom, and each of $X^1$ and $X^2$, which may be the same or different, is a halogen atom or a group represented by the formula $R^9SO_3$ (wherein $R^9$ is a methyl group; a trifluoromethyl group, a trichloromethyl group; a phenyl group or a p-methylphenyl group) are more particularly preferred.

The compound represented by the formula 1 may contain an asymmetric carbon atom. In other words, the compound of the present invention represented by the formula 1 covers mixtures and isolates of various optical isomers such as optically active compounds and racemates.

By virtue of the presence of the amine residue, the compound of the formula 1 can behave as an amine derivative, by forming addition products with acids. Consequently, the compound represented by the formula 1 may be in the form of a salt with a mineral acid such as hydrochloric acid, hydrobromic acid, sulfuric acid or phosphoric acid, or an organic acid such as formic acid, acetic acid, oxalic acid, malonic acid, succinic acid, fumaric acid, maleic acid, lactic acid, malic acid, tartaric acid, citric acid, methanesulformic acid, trifluoromethanesulformic acid, toluenesulformic acid or benzenesulfonic acid, resulting from addition of such an acid. Further, the compound represented by the formula 1 may be in the form of various hydrates, solvates or polymorphic crystals.

Now, preparation of the compound represented by the formula 1 is described below. The compound of the present invention is obtainable by various methods, and the method of the present invention is by no means restricted to the following production methods which are give just as examples. In the reaction formulae, Ac denotes an acetyl group, and Boc denotes a t-butoxycarbonyl group.

The first production method follows the following reaction formula 1 (wherein $R^1$, $Z^1$, $X^2$, l, m and n are the same as defined previously, each of A and D, which may be the same or different, is a group represented by the formula —$NR^3$— (wherein $R^3$ is a hydrogen atom, a lower alkyl group or a lower alkyl group substituted with a halogen atom), a group represented by the formula —$N^+R^4R^5$. $Q^-$—(wherein each of $R^4$ and $R^5$, which may be the same or different, is a lower alkyl group or a lower alkyl group substituted with a halogen atom, and Q is a halogen atom, a group represented by the formula $R^6COO$ (wherein $R^6$ is a lower alkyl group or a lower alkyl group substituted with a halogen atom) or a group represented by the formula $R^7SO_3$ (wherein $R^7$ is a lower alkyl group, a lower alkyl group substituted with a halogen atom or a phenyl group which may be substituted with a lower alkyl group)), an oxygen atom or a sulfur atom).

The compound of the formula 1 (compound II in the reaction formula 1) is obtainable by reacting compound 4 and compound 5 in a polar solvent such as such as DMF (dimethylformamide), DMSO (dimethyl sulfoxide) or methanol in the presence or absence of a base at from 0° C. to 150° C. for from several minutes to 30 hours. Compound 4 is obtainable by reacting compound 3 and compound 6 in a polar solvent such as DMF (dimethylformamide), DMSO (dimethyl sulfoxide) or methanol in the presence or absence of a base at from 0° C. to 150° C. for several minutes to 30 hours. Compound 3 is synthesized from compound 2 by heating with an acid such as hydrobromic acid or hydrochloric acid. Compound 2 is obtainable by reacting the corresponding diiode compound and compound 1 in a polar solvent such as DMF (dimethylformamide), DMSO (dimethyl sulfoxide) or methanol or in a solvent-free system at from room temperature to 200° C. for several minutes to 30 hours.

Examples of the base used in the production method represented by the reaction formula 1 include sodium hydroxide, potassium hydroxide, potassium carbonate, sodium carbonate, sodium hydrogen carbonate, triethylamine, pyridine, ethyldiisopropylamine and sodium hydride.

Reaction formula 1

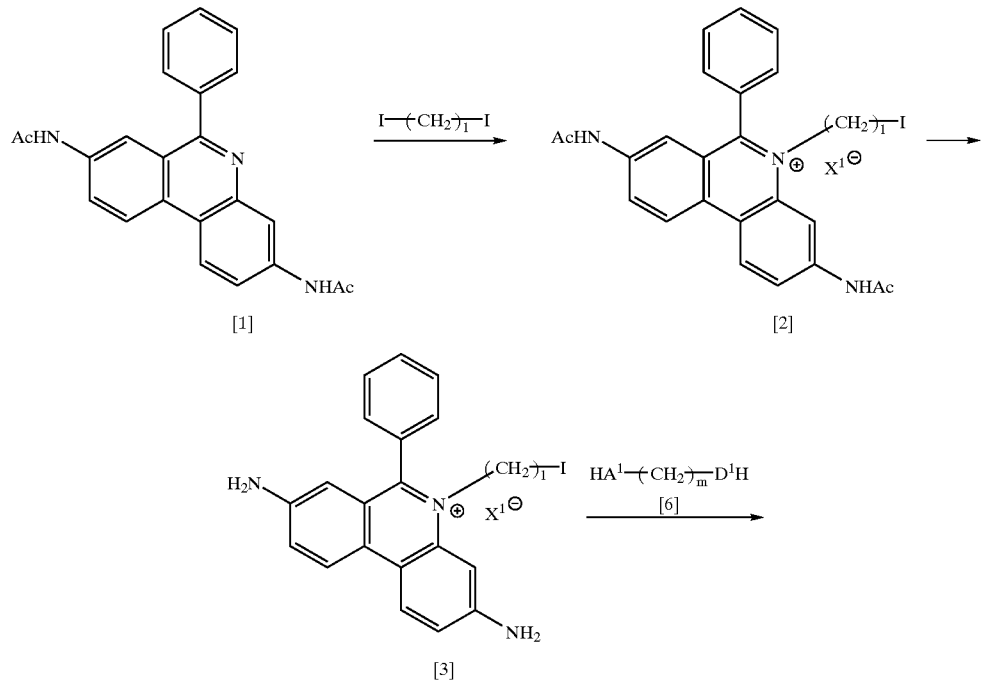

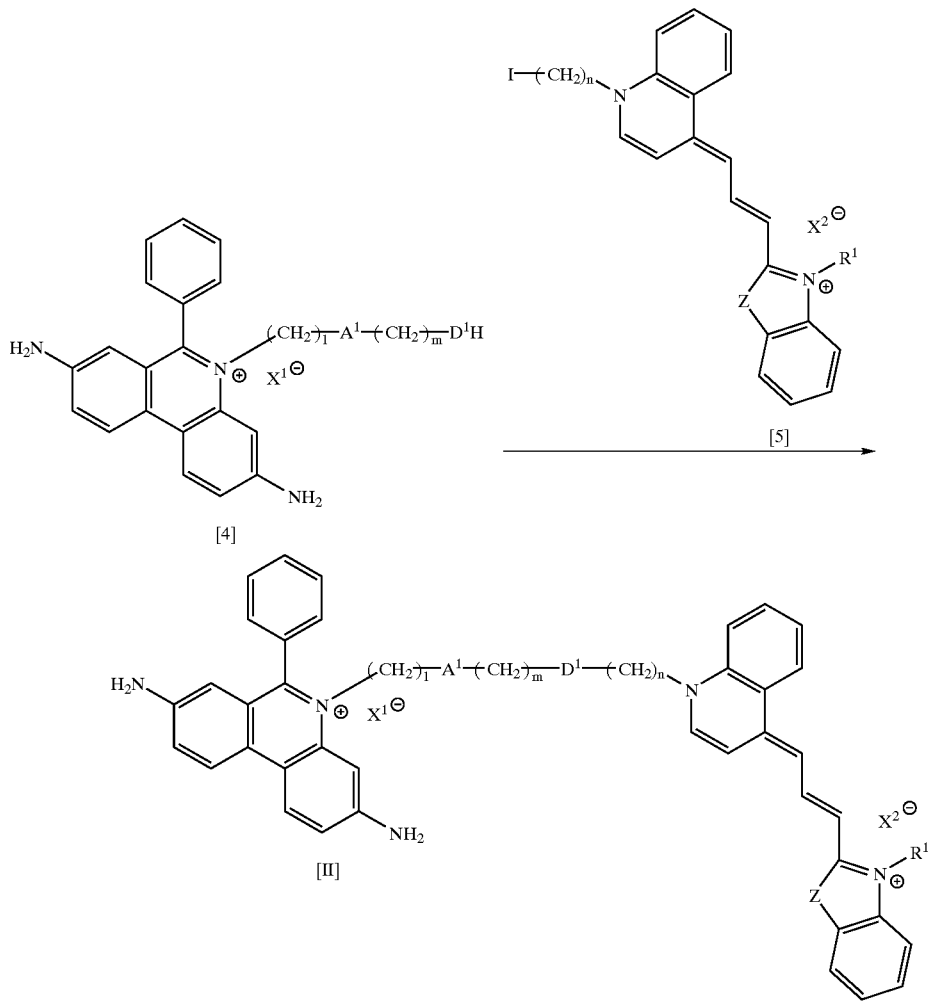

The second production method follows the following reaction formula 2 (wherein $R^1$, $A^1$, $D^1$, Z, $X^1$, $X^2$, l, m and n are the same as defined previously).

The compound of the formula 1 (compound II in the above reaction formula 2) is obtainable by heating compound 9 with an acid such as hydrobromic acid or hydrochloric acid. Compound 9 is obtainable by reacting compound 7 and compound 2 in a polar solvent such as DMF (dimethylformamide), DMSO (dimethyl sulfoxide) or methanol in the presence or absence of a base at from 0° C. to 150° C. for several minutes to 30 hours. Compound 7 is obtainable by reacting compound 5 and compound 6 in a polar solvent such as DMF (dimethylformamide), DMSO (dimethyl sulfoxide) or methanol or in a solvent-free system in the presence or absence of a base at from 0° C. to 150° C. for several minutes to 30 hours. Compound 9 is also obtainable by reacting compound 10 and compound 5 in a polar solvent such as DMF (dimethylformamide), DMSO (dimethyl sulfoxide) or methanol in the presence or absence of a base from 0° C. to 150° C. for several minutes to 30 hours. Compound 10 is obtainable by compound 2 and compound 6 in a polar solvent such as DMF (dimethylformamide), DMSO (dimethyl sulfoxide) or methanol in the presence or absence of a base from 0° C. to 150° C. for several minutes to 30 hours.

Examples of the base used in the process represented by the reaction formula 2 include sodium hydroxide, potassium hydroxide, potassium carbonate, sodium carbonate, sodium hydrogen carbonate, triethylamine, pyridine, ethyldiisopropylamine and sodium hydride.

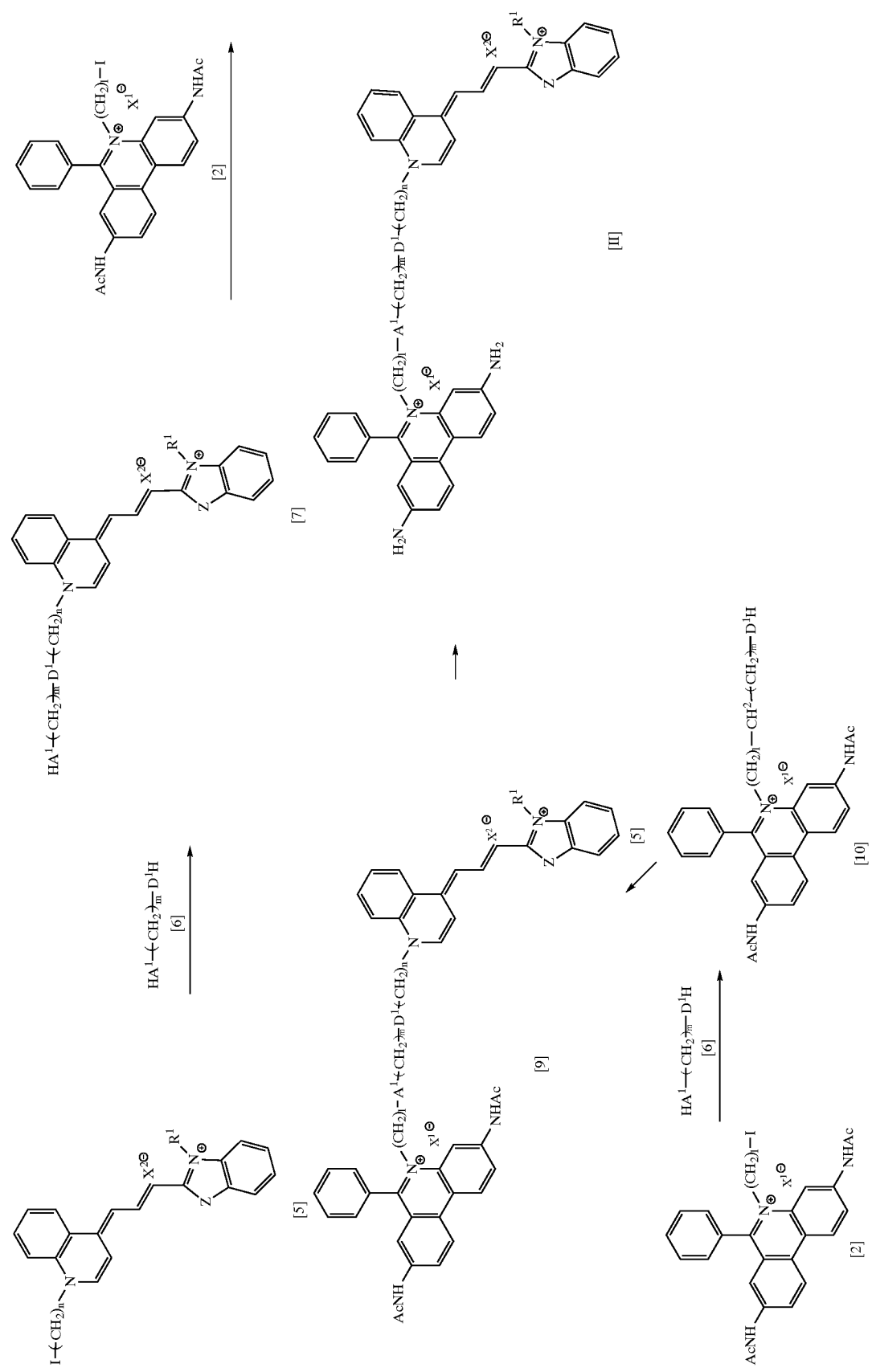

The third production method follows the following reaction formula 3 (wherein $R^1, A^1, D^1, Z, X^1, X^2, l, m$ and $n$ are the same as defined previously).

The compound of the formula 1 (compound II in the reaction formula 3) is obtainable by reacting compound 7 and compound 3 in a polar solvent such as DMF (dimethylformamide), DMSO (dimethyl sulfoxide) or methanol in the presence or absence of a base at from 0° C. to 150° C. for several minutes to 30 hours. Examples of the base used in the process represented by the reaction formula 3 include sodium hydroxide, potassium hydroxide, potassium carbonate, sodium carbonate, sodium hydrogen carbonate, triethylamine, pyridine, ethyldiisopropylamine and sodium hydride.

alkyl group or a lower alkyl group substituted with a halogen atom), an oxygen atom or a sulfur atom).

The compound of the formula 1 (compound III in the reaction formula 4) is obtainable by heating compound 14 with an acid hydrobromic acid or hydrochloric acid. Compound 14 is obtainable by reacting compound 13 and compound 1 in a polar solvent such as such as DMF (dimethylformamide), DMSO (dimethyl sulfoxide) or methanol in the presence or absence of a base at from 0° C. to 150° C. for from several minutes to 30 hours.

Compound 13 is obtainable from 4-methylquinoline via compound 12 by a conventional method (J. Am. Chem. Soc., 64, 199 (1942)).

Reaction formula 3

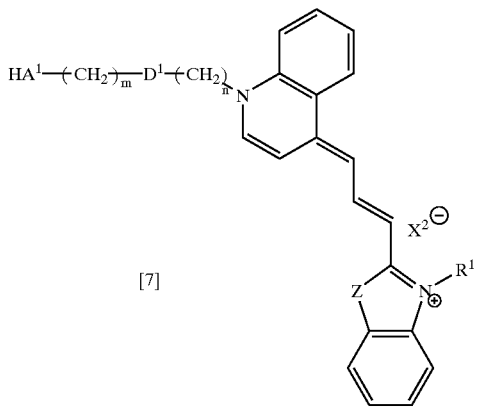
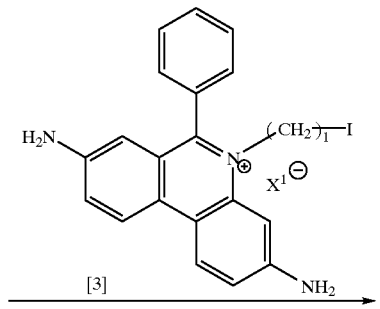
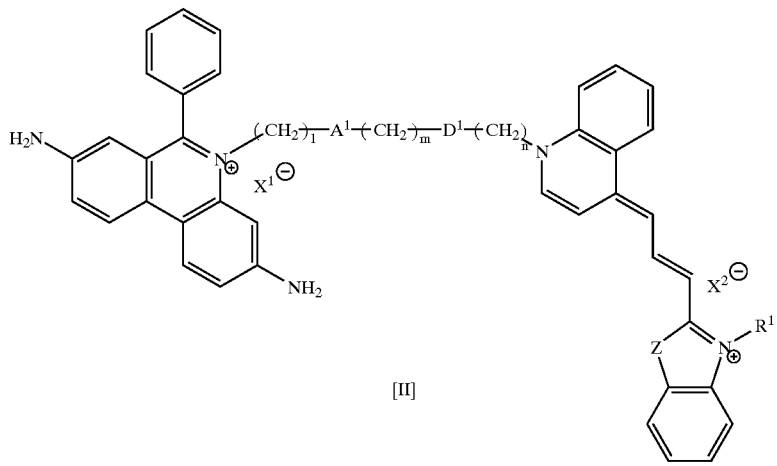

The fourth production method follows the following reaction formula 4 (wherein $R^1, Z, X, X^1, l, m$ and $n$ are the same as defined previously, and each of A and D which may be the same or different, is a group represented by the formula —$CHR^2$— (wherein $R^2$ is a hydrogen atom, a lower Examples of the base used in the production method represented by the reaction formula 4 include sodium hydroxide, potassium hydroxide, potassium carbonate, sodium carbonate, sodium hydrogen carbonate, triethylamine, pyridine, ethyldiisopropylamine and sodium hydride.

Reaction formula 4

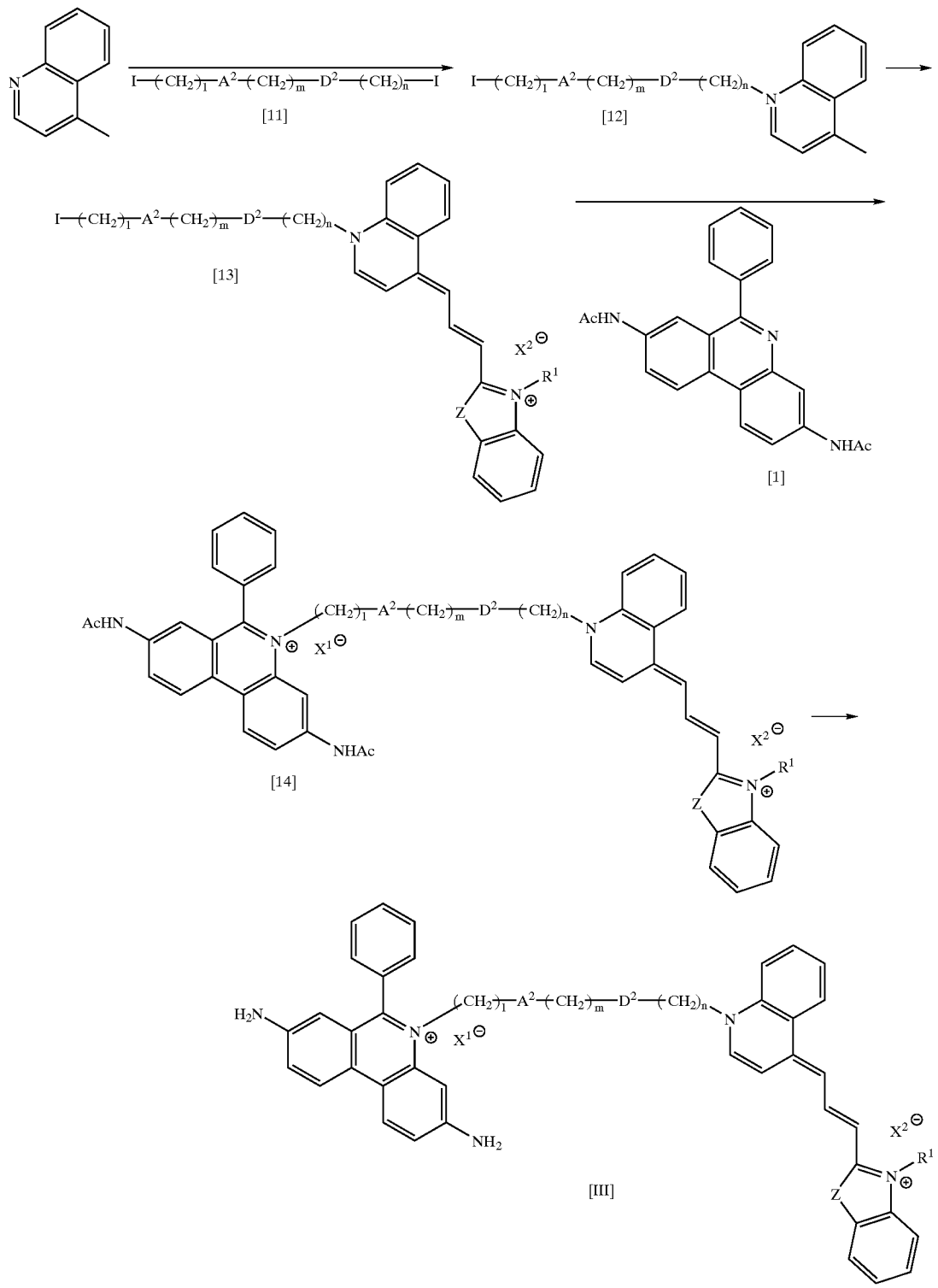

The fifth production method follows the following reaction formula 5 (wherein $R^1$, $A^1$, Z, $X^1$, $X^2$, l, m and n are the same as defined previously, $D^3$ is a group represented by the formula —$NR^3$— (wherein $R^3$ is a hydrogen atom, a lower alkyl group or a lower alkyl group substituted with a halogen atom), $D^4$ is a group represented by the formula —$NR^{10}$— (wherein $R^7$ is a hydrogen atom, a lower alkyl group or a lower alkyl group substituted with a halogen atom), a group represented by the formula —$N^+R^4R^5.Q^-$— (wherein each of $R^4$ and $R^5$, which may be the same or different, is a lower alkyl group or a lower alkyl group substituted with a halogen atom, and Q is a halogen atom, a group represented by the formula R[6]COO (wherein R[6] is a lower alkyl group or a lower alkyl group substituted with a halogen atom) or a group represented by the formula R[7]SO₃ (wherein R[7] is a lower alkyl group, a lower alkyl group substituted with a halogen atom or a phenyl group which may be substituted with a lower alkyl group)), X[3] is a halogen atom, or a group represented by the formula R[9]SO₃ (wherein R[9] is a lower alkyl group, a lower alkyl group substituted with a halogen atom or a phenyl group which may be substituted with a lower alkyl group), and R11 is a lower alkyl group or a lower alkyl group substituted with a halogen atom).

The compound of the formula 1 (compound IV in the reaction formula 5) can be synthesized by heating compound 17 with an acid such as hydrobromic acid or hydrochloric acid. Compound 17 is obtainable by reacting compound 16 and an alkylating agent 20 in a polar solvent such as such as DMF (dimethylformamide), DMSO (dimethyl sulfoxide) or methanol in the presence or absence of a base at from 0° C. to 150° C. for from several minutes to 30 hours. Examples of the base used in the production method represented by the reaction formula 5 include sodium hydroxide, potassium hydroxide, potassium carbonate, sodium carbonate, sodium hydrogen carbonate, triethylamine, pyridine, ethyldiisopropylamine and sodium hydride.

Reaction formula 5

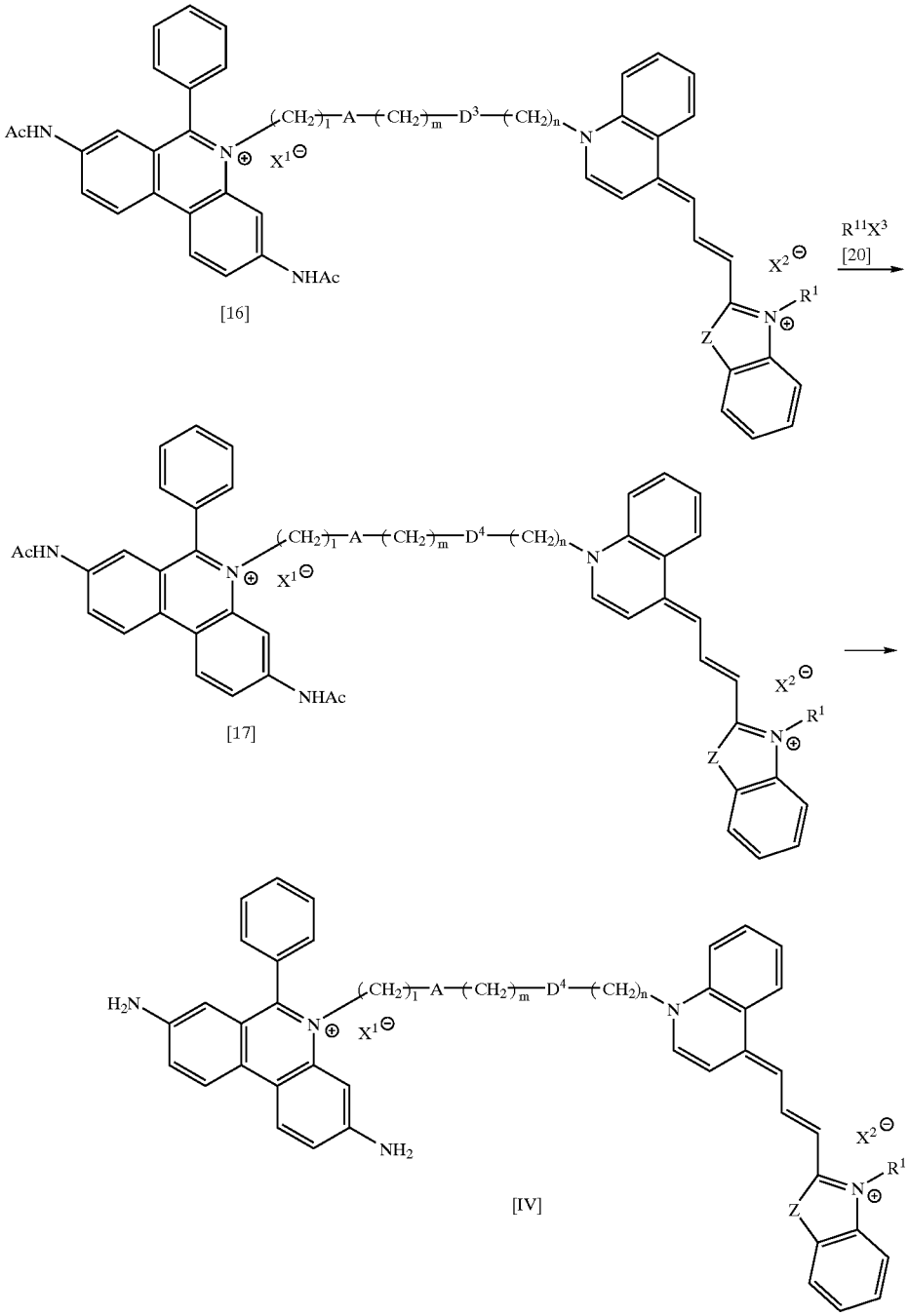

The sixth production method follows the following reaction formula 6 (wherein $R^1$, $R^{11}$, A, $D^3$, $D^4$, Z, $X^1$, $X^2$, $X^3$, l, m and n are the same as defined previously).

The compound of the formula 1 (compound IV in the reaction formula 6) is obtainable by reacting compound V and an alkylating agent 20 in a polar solvent such as such as DMF (dimethylformamide), DMSO (dimethyl sulfoxide) or methanol in the presence or absence of a base at from 0° C. to 150° C. for from several minutes to 30 hours. Examples of the base used in the production method represented by the reaction formula 6 include sodium hydroxide, potassium hydroxide, potassium carbonate, sodium carbonate, sodium hydrogen carbonate, triethylamine, pyridine, ethyldiisopropylamine and sodium hydride.

a halogen atom) or a group represented by the formula —$N^+R^4R^5.Q^-$— (wherein each of $R^4$ and $R^5$, which may be the same or different, is a lower alkyl group or a lower alkyl group substituted with a halogen atom, and Q is a halogen atom, a group represented by the formula $R^6COO$ (wherein $R^6$ is a lower alkyl group or a lower alkyl group substituted with a halogen atom) or a group represented by the formula $R^7SO_3$ (wherein $R^7$ is a lower alkyl group, a lower alkyl group substituted with a halogen atom or a phenyl group which may be substituted with a lower alkyl group))).

The compound of the formula 1 (compound VII in the reaction formula 7) can be synthesized by heating compound 19 with an acid such as hydrobromic acid or hydrochloric acid. Compound 19 is obtainable by reacting compound 18

Reaction formula 6

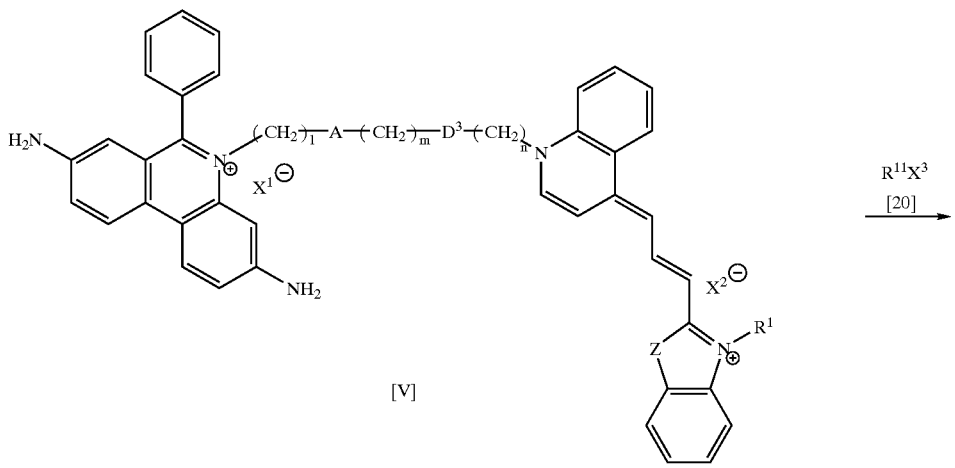

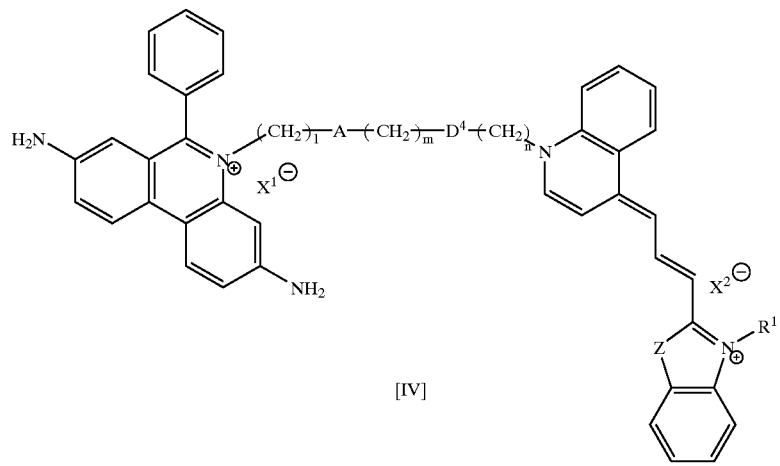

The seventh production method follows the following reaction formula 7 (wherein $R^1$, $R^{11}$, D, Z, $X^1$, $X^2$, $X^3$, l, m and n are the same as defined previously, $A^3$ is a group represented by the formula —$NR^3$— (wherein $R^3$ is a hydrogen atom, a lower alkyl group or a lower alkyl group substituted with a halogen atom), $A^4$ is a group represented by the formula —$NR^{10}$— (wherein $R^{10}$ is a hydrogen atom, a lower alkyl group or a lower alkyl group substituted with and an alkylating agent 20 in a polar solvent such as such as DMF (dimethylformamide), DMSO (dimethyl sulfoxide) or methanol in the presence or absence of a base at from 0° C. to 150° C. for from several minutes to 30 hours. Examples of the base used in the production method represented by the reaction formula 5 include sodium hydroxide, potassium hydroxide, potassium carbonate, sodium carbonate, sodium hydrogen carbonate, triethylamine, pyridine, ethyldiisopropylamine and sodium hydride.

Reaction formula 7

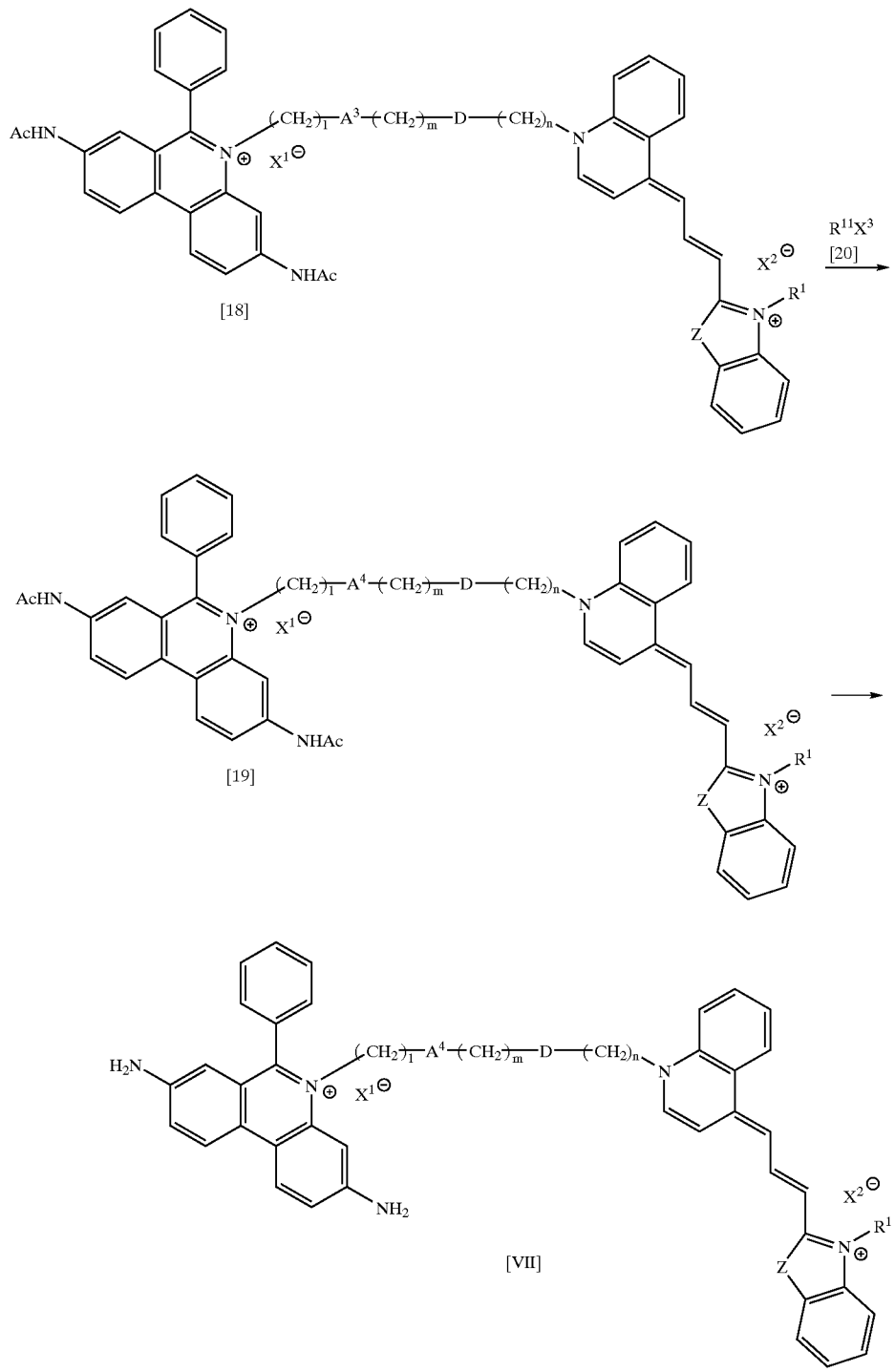

The eighth production method follows the following reaction formula 8 (wherein $R^1$, $R^{11}$, $A^3$, $A^4$, D, Z, $X^1$, $X^2$, $X^3$, l, m and n are the same as defined previously).

The compound of the formula 1 (compound VII in the reaction formula 8) is obtainable by reacting compound VI and an alkylating agent 20 in a polar solvent such as such as DMF (dimethylformamide), DMSO (dimethyl sulfoxide) or methanol in the presence or absence of a base at from 0° C. to 150° C. for from several minutes to 30 hours. Examples of the base used in the production method represented by the reaction formula 6 include sodium hydroxide, potassium hydroxide, potassium carbonate, sodium carbonate, sodium hydrogen carbonate, triethylamine, pyridine, ethyldiisopropylamine and sodium hydride.

Reaction formula 8

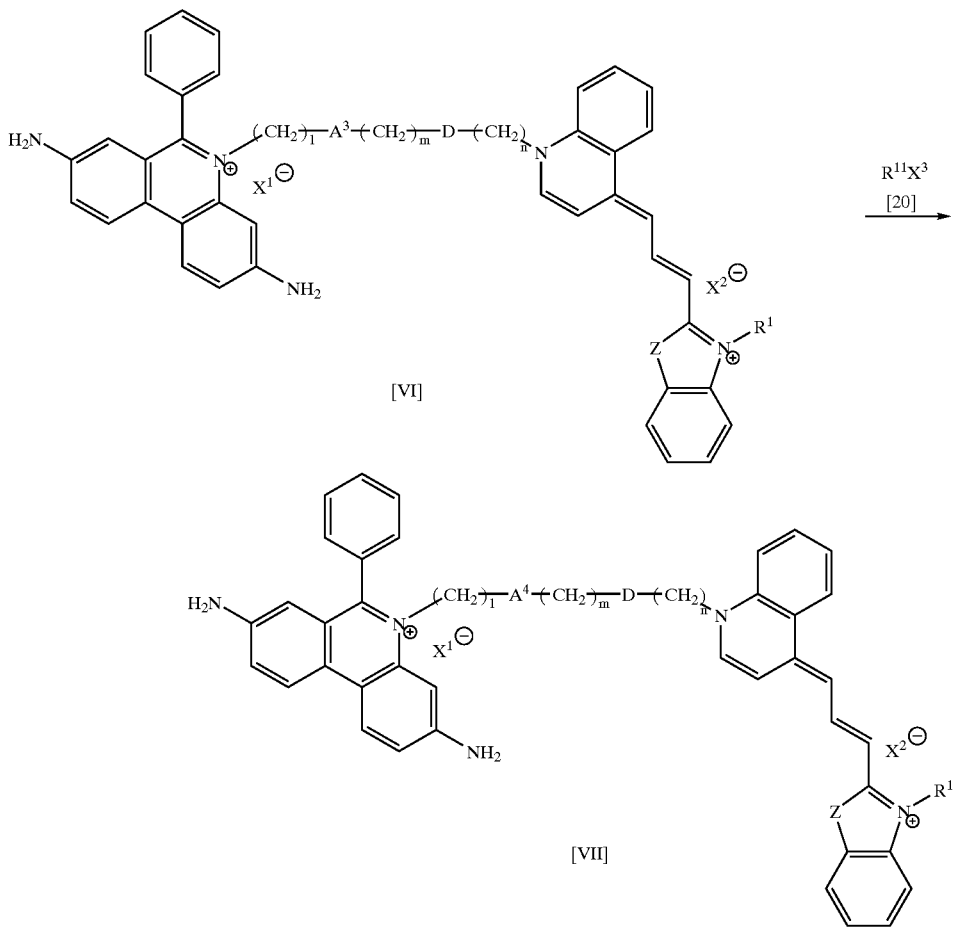

The product of each step in each reaction formula can be isolated or purified, if necessary, by appropriately using conventional purification techniques such as chromatography, recrystallizaton, precipitation or distillation singly or in combination. In some cases, the product of each step can be used in the subsequent reaction without isolation or purification.

The compound represented by the formula 1 has such a structure that an ethidium bromide (phenylphenanthridine) derivative which can get excited at a broad range of wavelengths and a thiazole derivative having a fluorescent peak around 660 nm or an oxazole derivative having a fluorescent peak around 630 nm are linked via a linker. Therefore, when the compound is irradiated with an excitation radiation, the ethidium derivative gets excited firstly. The excitation energy transfers to the thiazole or oxazole derivative, and the thiazole or oxazole derivative excited as the result of the so-called fluorescent energy transfer, emits fluorescence.

Ethidium bromide is a compound having an absorption peak at wavelengths around 535 nm but shows an absorption spectrum having a broad peak. Therefore, the compound represented by the formula 1 can get excited at a broad range of wavelengths. Because the thiazole derivative emits fluorescence having a sharp peak, when the compound represented by the formula 1 is excited, the fluorescence having a sharp peak emitted from the thiazole derivative is observed. Therefore, the compound represented by the formula 1 enables detection or quantification of a nucleic acid anticipated to be contained in a sample.

For example, when the compound of the formula 1 is mixed with a double-stranded nucleic acid, the compound of the formula 1 intercalates into the complementary double strand of the nucleic acid and shows remarkable fluorescence enhancement (the fluorescence intensity of a mixed aqueous solution of the compound of the formula 1 and a double-stranded nucleic acid is remarkably greater than that of an aqueous solution of the compound of the formula 1 alone). Therefore, the compound of the formula 1 can detect a double-stranded DNA, a double-stranded RNA or a DNA/RNA hybrid or any combination of them in a sample. Further, the amount of the nucleic acid in the sample can be determined from comparison with a known amount of another double-stranded nucleic acid.

The compound of the formula 1 may be linked to a single-stranded oligonucleotide (preferably DNA) complementary to a specific nucleic acid sequence in a nucleic acid (target nucleic acid) by a chemical bond to make a nucleic acid probe. In the nucleic acid probe, it is particularly preferred that the compound of the formula 1 is so linked to the single-stranded oligonucleotide that the compound can intercalates into the double strand formed by hybridization of the target nucleic acid and the single-stranded oligonucleotide. The presence of the single-stranded oligonulecotide imparts sufficient specificity for the target nucleic acid to the nucleic acid probe. Besides, because the intercalation of the compound of the formula 1 into the double-strand formed by hybridization with the target nucleic acid in a sample leads to remarkable fluorescence enhancement, assay of the target nucleic acid in a closed vessel is possible without separation of the nucleic acid probe which is not hybridized with the target nucleic acid. The compound of the formula 1 may be so linked by any method without any special restriction so that it can intercalates into the double-strand formed by hybridization of the target nucleic acid and the single-stranded oligonucleotide, but it is preferred to link the compound of the formula 1 to a phosphorus atom in the oligonucleotide (preferably DNA) oligomer by a chemical bond via a linker. Although there is no any particular restriction on the linker, it is possible to preliminarily introducing a conventional bifunctional crosslinking linker, SPDP (S-pyridyldithiopropanyl succinimide), into an aminated DNA oligomer, while introducing a SH-reactive functional group derived from another compound into the compound of the formula 1, and reacting them.

The nucleic acid probe of the present invention may be present in a reaction solution used for amplification of a target RNA. Therefore, the nucleic acid probe enables amplification and assay of the target RNA in a closed vessel in one step (assay of the target RNA in a vessel previously loaded with the necessary reagents without addition of any reagents or separation of redundant reagents). For the amplification itself, the procedures disclosed in Patent No. 2650159, EP-A-373960, Japanese Unexamined Patent Publication JP-A-8-211050 and the like may be used.

The fluorescent spectrum of the compound of the—formula 1 does not overlap with the fluorescent spectrum of oxazole yellow, which is known as a fluorescent intercalative dye. The combined use of the compound of the formula 1 with a known fluorescent intercalative dye whose fluorescent spectrum does not overlap with that of the compound of the formula 1 enables conventionally unachievable simultaneous assay of at least two target RNAs. Oxazole yellow is known to have an absorption maximum at 488 nm and a fluorescence maximum at 510 nm. The compound of the formula 1 can also be excited by a radiation at 488 nm, but emits fluorescence having a spectrum with a maximum at 660 nm. By virtue of the difference as large as 150 nm between the wavelengths of their maximum fluorescence, their fluorescent spectra do not overlap. The combination of the compound of the formula 1 and oxazole yellow is advantageous in that because both of them can be excited by radiation at about 470 nm, they can share an inexpensive and small light emitting diode as an excitation radiation source.

In the above-mentioned assay method using the compound of the formula 1 and a conventionally known fluorescent intercalative dye, both dyes are used in the form of nucleic acid probes obtained by linking them to single-stranded oligonucleotides (preferably DNAs). Specifically, the method comprises a step of amplifying the target RNAs simultaneously in the presence of probes which are complementary to the respective amplification products and labeled with different fluorescent intercalative dyes, and a step of measuring the change in fluorescence intensity resulting from intercalation into the double strands formed by hybridization of the amplification products and the probes, wherein one of the fluorescent intercalative dyes is the compound represented by the formula 1, and the other is a fluorescent intercalative dye which is excited by a radiation at the same wavelength as the compound represented by the formula 1 but emits fluorescence at a wavelength different from the wavelength of the fluorescence from the compound represented by the formula 1. More specifically, the method is used for measurement of at least one RNA (target RNA) having a specific nucleic acid sequence in a sample and comprises a step of amplifying the target RNA and a known amount of a standard nucleic acid added to the sample simultaneously in the presence of probes which are complementary to the respective amplification products and labeled with different fluorescent intercalative dyes, a step of measuring the fluorescence intensity which has changed due to intercalation of the fluorescent intercalative dyes into the double strands formed by hybridization of the amplification products and the probes, and comparing the fluorescence intensity with that measured similarly by using similar reagents in the presence of a known amount of the standard nucleic acid (an amplification curve showing fluorescence enhancement accompanying the progress of the amplification), wherein one of the fluorescent intercalative dyes is the compound represented by the formula 1, and the other is a fluorescent intercalative dye which is excited by a radiation at the same wavelength as the compound represented by the formula 1 but emits fluorescence at a wavelength different from the wavelength of the fluorescence from the compound represented by the formula 1. These methods are applicable to biological samples such as serum, plasma, humor, urine and feces, possibly microbially contaminated samples from food, rooms, river water and sea water, and samples of nucleic acid extracts from those.

Although the amplification method is not limited, it is preferred that RNA production proceeds almost isothermally.

As mentioned above, oxazole yellow, which is known as a fluorescent intercalative dye, can be excited by radiation at the same wavelength but emits a fluorescent radiation having a different wavelength. Therefore, oxazole yellow is mentioned as a preferable example of the fluorescent intercalative dye used in the above-mentioned methods. The combined use of the compound of the formula 1 and oxazole yellow is advantageous in that both of them can be excited by a radiation at a wavelength of from 450 to 500 nm from a single excitation light source.

Among the above-mentioned methods, the method of measuring at least two target nucleic acid simultaneously makes it possible to detect or quantify plural viruses, plural microbial RNAs, plural specific sequences in one RNA as target nucleic acids in a short time. Among the above-mentioned methods, because the method in which a target nucleic acid is amplified and measured simultaneously with a standard nucleic acid added to a sample, can avoid the problem of so-called false positive results resulting from hindrances to the amplification reaction such as deactivation of a certain enzyme involved in the reaction and degradation of substrates or primers, it is possible to provide a method applicable to clinical diagnosis which requires high reliability. When a nucleic acid extract from a sample to which a standard nucleic acid has been added is used as a sample for the amplification, it is possible to not only check if a target nucleic acid is being amplified successfully, but also determine if the extraction was successful or determine the extraction efficiency.

in the presence of dT30mer (0.04 nmol) and dA30mer (0.04 nmol) at an excitation wavelength of 488 nm.

Figure 2:
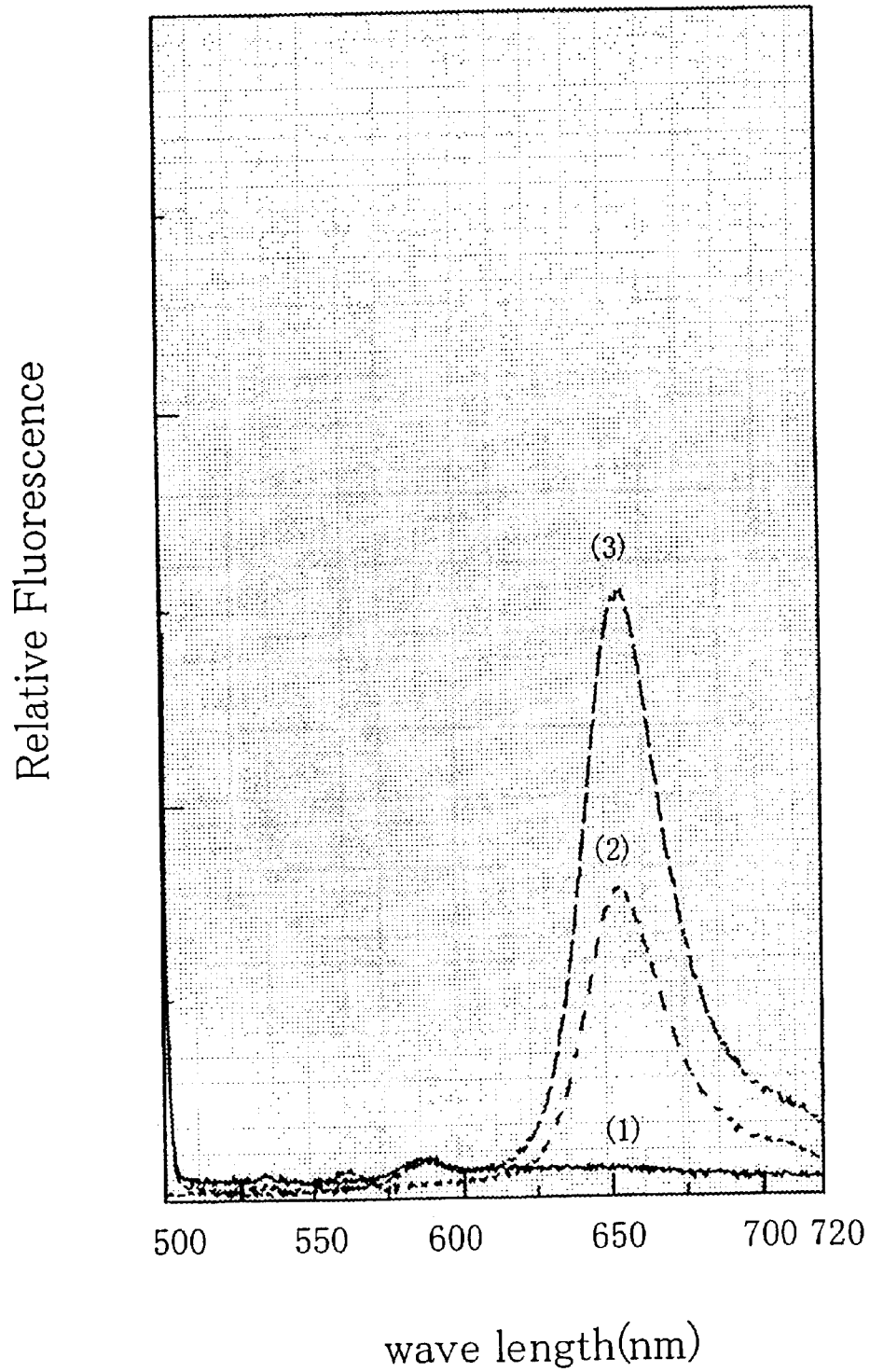

FIG. 2 shows the fluorescent spectra of compound 2 obtained in Example 6 (1) in the absence of a double-stranded nucleic acid at an excitation wavelength of 488 nm, (2) in the presence of dT30mer (0.04 nmol) and dA30mer (0.04 nmol) at an excitation wavelength of 470 nm, and (3) in the presence of dT30mer (0.04 nmol) and dA30mer (0.04 nmol) at an excitation wavelength of 488 nm.

Figure 3:
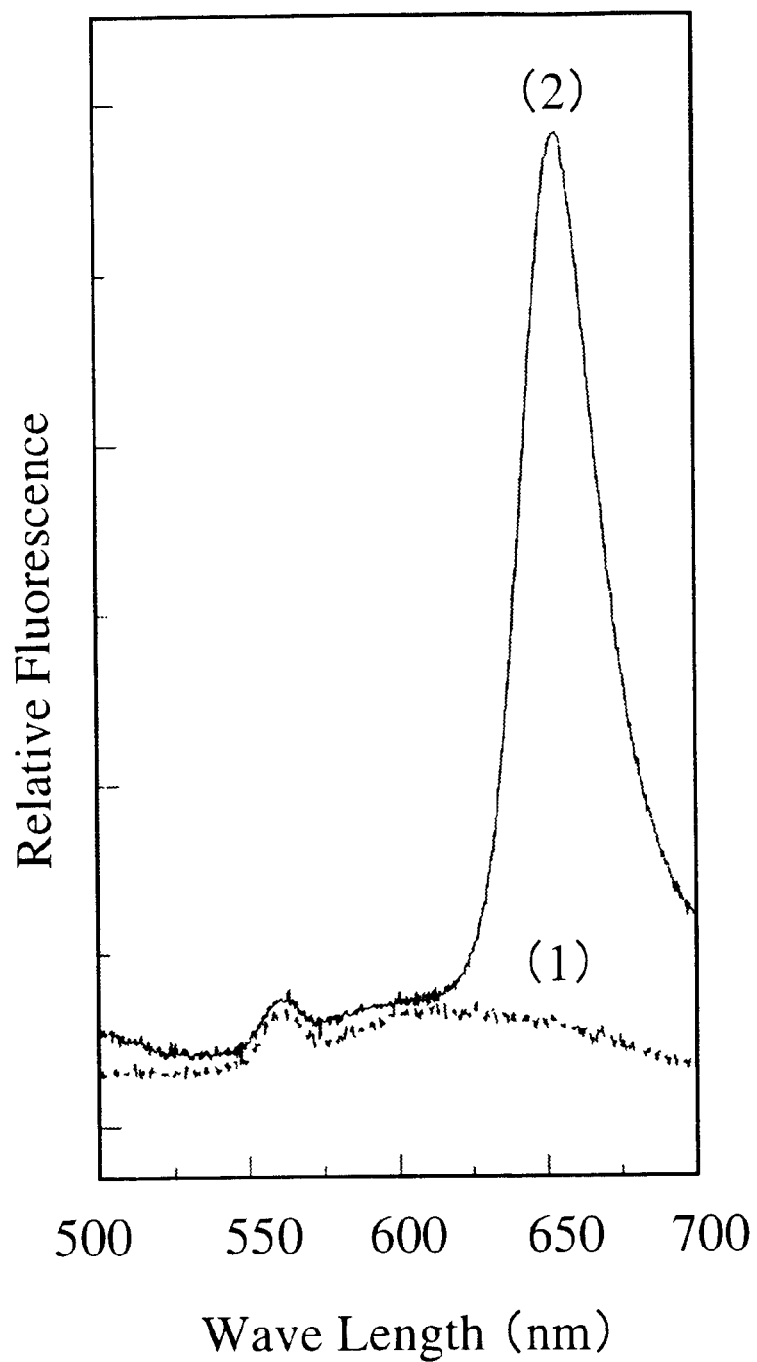

FIG. 3 shows the fluorescent spectra of compound 16c (2.5 μM) obtained in Example 9 (1) in the absence of a double-stranded nucleic acid at an excitation wavelength of 470 nm, and (2) in the presence of dT30mer (0.25 μM) and dA30mer (0.25 μM) at an excitation wavelength of 470 nm.

Figure 4:
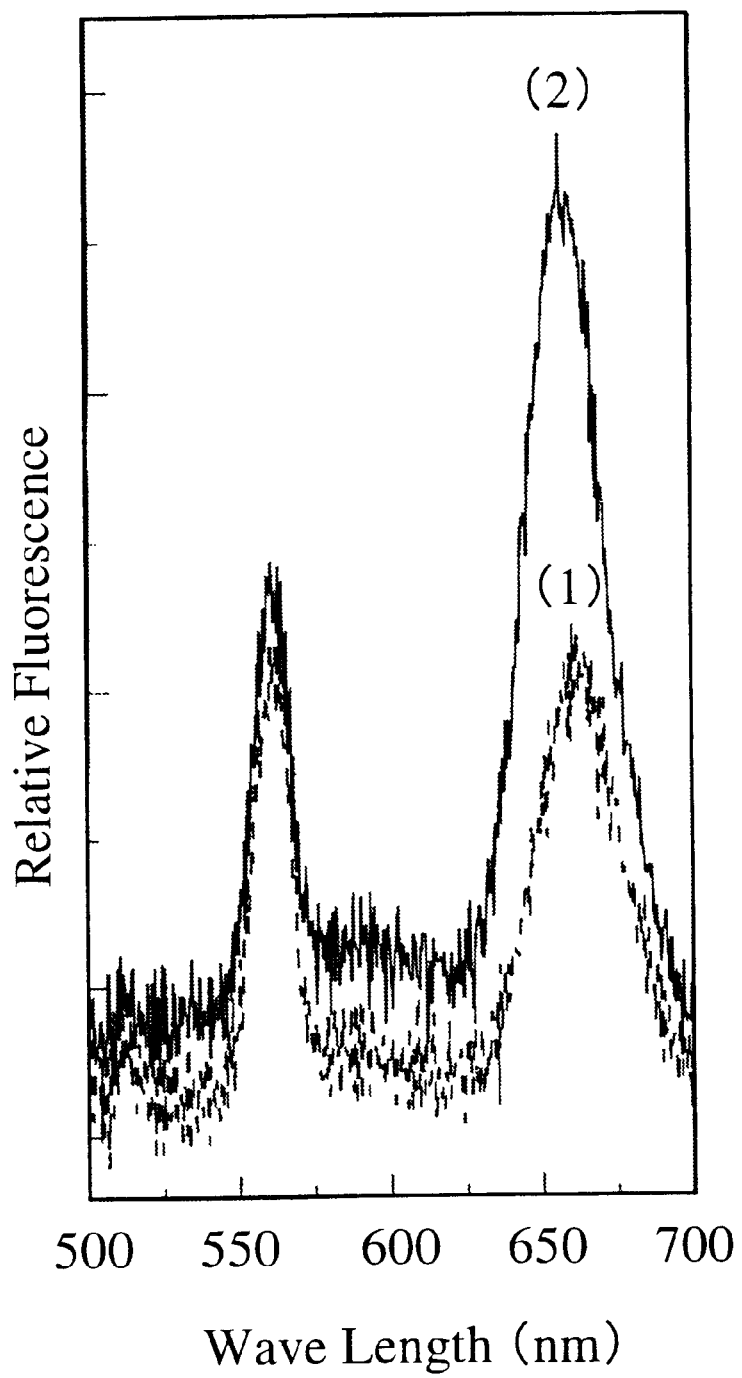

FIG. 4 shows the fluorescent spectra of compound 18 (1 μM) obtained in Example 10 (1) in the absence of a target nucleic acid at an excitation wavelength of 470 nm, and (2) in the presence of the target nucleic acid (1 μM) at an excitation wavelength of 470 nm.

Now, the present invention is described in further detail by reference to Examples, but the present invention is by no means restricted to these specific Examples.

EXAMPLE 1

A compound of the formula 1 was prepared by the following method. The reaction procedure is represented later by the reaction formula 9.
(1) Preparation of Compound 1 in the Reaction Formula 9

3,8-diamino-6-phenylphenanthridine (1.2 g) in acetic acid (7 ml) was stirred with acetic anhydride (3.3 ml) for 1.5 hours. After addition of water (26 ml), 28% aqueous ammonia (20 ml) was added dropwise. The resulting solid was recovered by filtration, washed with water and dried. The resulting crude product was dissolved in hot ethanol, and allowed to stand at room temperature. The resulting solid was recovered by filtration as the desired compound 1 in a yield of 0.78 g.

Compound 1 was a pale brown solid showing the following NMR characteristics.

1H—NMR (500 MHz, DMSO-d6, δ ppm) 2.05 (bs, 3H), 2.13 (bs, 3H), 7.42–7.95 (m, 6H) 8.10–8.50 (m, 3H), 8.55–8.82 (m, 2H) 10.30 (bs, 2H)
(2) Preparation of Compound 2 in the Reaction Formula 9

A suspension of Compound 1 (500 mg) thus obtained in 1,3-diiodopropane (10 ml) was stirred at 155° C. for 6 hours, then allowed to cool and concentrated under reduced pressure made by a vacuum pump. The resulting crude product was dissolved in hot methanol and allowed to stand at room temperature. The resulting solid was recovered by filtration as the desired compound 2 in a yield of 320 mg.

Compound 2 was a pale brown solid showing the following NMR characteristics.

1H—NMR (500 MHz, DMSO-d6, δ ppm) 2.02 (s, 3H), 2.21 (s, 3H), 2.36–2.45 (m, 2H) 3.26 (t, J=6.5 Hz, 2H), 3.33 (s, 3H) 4.67 (t, J=8.5 Hz, 2H), 7.72–7.82 (m, 5H) 7.88 (d, J=2.0 Hz, 1H) 8.12 (dd, J=1.5 Hz, 9.0 Hz, 1H) 8.42 (dd, J=2.0 Hz, 9.0 Hz, 1H) 8.92 (s, 1H), 9.03 (d, J=9.0 Hz, 1H) 9.09 (d, J=9.5 Hz, 1H), 10.5 (s, 1H), 10.8 (s, 1H)
(3) Preparation of Compound in the Reaction Formula 9

Firstly, compound 3 was prepared by the known method (J. Am. Chem. Soc., 64, 199 (1942)). Compound 3 (74 mg) in DMF (0.5 ml) was stirred with N,N,N'-trimethyl-1,3-propanediamine (0.2 ml) at room temperature for 1 hour, and it was concentrated under reduced pressure made by a vacuum pump. The resulting crude product gave 60 of the desired compound 4 after purification by column chromatography (aminated silica gel NH—DM1020, product name, Fuji silycia Co. Ltd.; eluent chloroform/methanol=95/5).

Compound 4 showed the following NMR characteristics.

1H—NMR (500 MHz, DMSO-d6, δppm) 1.48–1.55 (m, 2H), 1.92–2.01 (m, 2H), 2.11 (s, 6H) 2.12 (s, 3H), 2.19 (t, J=7.5 Hz, 2H) 2.28 (t, J=7.0 Hz, 2H), 2.34 (t, J=6.5 Hz, 2H) 3.74 (s, 3H), 4.47 (t, J=6.5 Hz, 2H) 6.49 (d, J=12.0 Hz, 1H), 7.11 (d, J=13.5 Hz, 1H) 7.31 (t, J=7.5 Hz, 1H), 7.49 (t, J=8.0 Hz, 1H) 7.59 (d, J=8.0 Hz, 1H), 7.71 (t, J=7.5 Hz, 1H) 7.84 (d, J=7.5 Hz, 1H), 7.88 (d, J=8.0 Hz, 1H) 7.95 (t, J=7.5 Hz, 1H), 8.09 (d, J=9.0 Hz, 1H) 8.15 (t, J=13.0 Hz, 1H), 8.39 (d, J=7.0 Hz, 1H) 8.47 (d, J=8.0 Hz, 1H)
(4) Preparation of the Compound of the Formula 1 ("Compound 1" in the Reaction Formula 9)

Compound 4 (20 mg) in DMF (1 ml) was stirred with compound 2 (22 mg) at 130° C. for 1 hour. After the reaction, it was concentrated under reduced pressure made by a vacuum pump to recover crude product 5. Crude product 5 thus obtained was dissolved in 47% aqueous hydrobromic acid and stirred at 170° C. for 1 hour. After the reaction, the crude product was recovered by concentration under reduced pressure. The crude product gave 6 mg of the desired compound of the formula 1 after purification by column chromatography (aminated silica gel NH-DM1020, product name, Fuji silycia Co. Ltd.; eluent chloroform/methanol=9/1).

The compound of the formula 1 ("compound 1" in the reaction formula 9) showed the following NMR characteristics.

1H—NMR (500 MHz, DMSO-d6, δ ppm) 1.79–1.90 (m, 2H), 1.92–2.01 (m, 2H) 2.05–2.14 (m, 2H), 2.15 (s, 3H), 2.23–2.42 (m, 8H) 3.04 (s, 6H), 3.74 (s, 3H), 4.35–4.45 (m, 2H) 4.52–4.60 (m, 2H), 5.91 (s, 1H), 6.22 (s, 1H) 6.42 (d, 1H), 6.54 (s, 1H), 7.04 (d, 1H), 7.20 (d, 1H) 7.31 (t, J=7.5 Hz, 1H), 7.45–8.15 (m, 13H) 8.32 (d, 1H), 8.42 (d, 1H), 8.54 (d, 2H)

Reaction formula 9

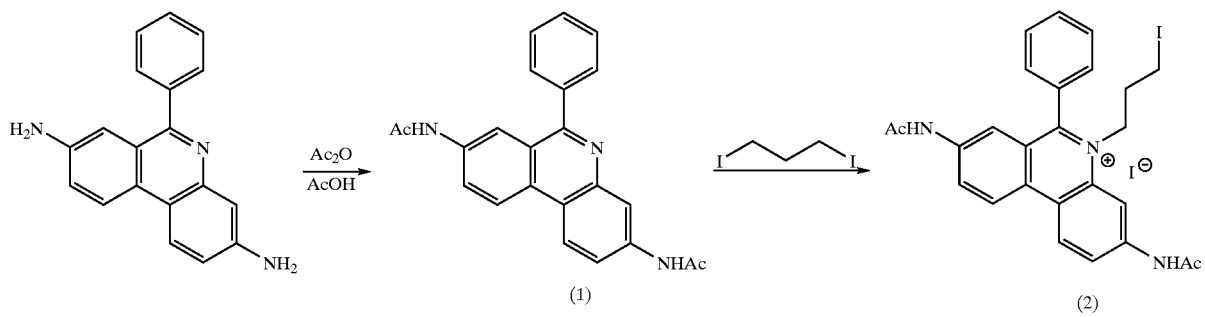

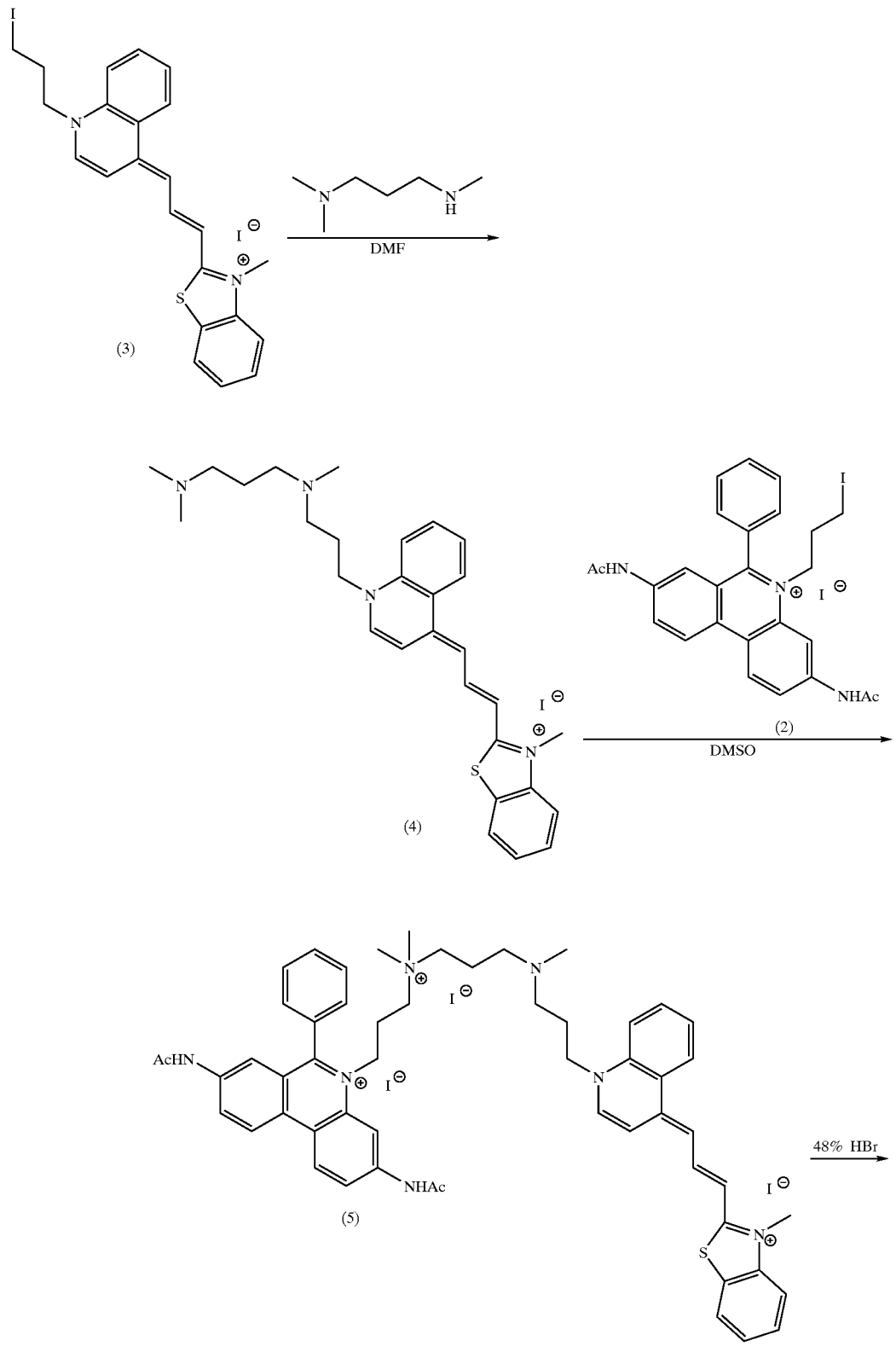

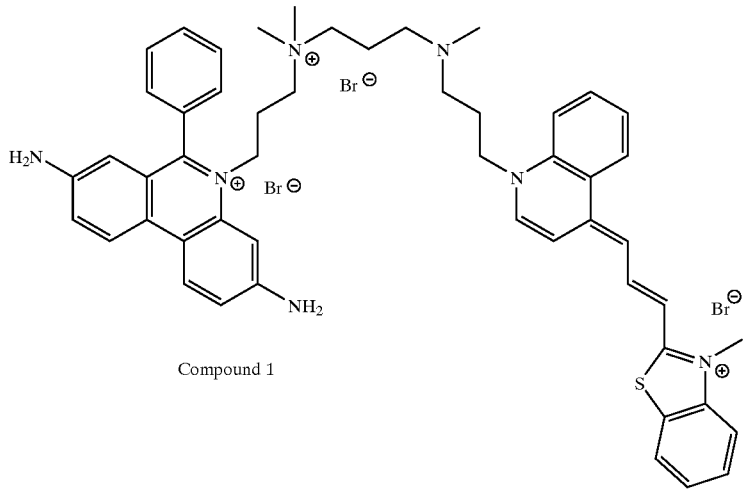

Compound 1

EXAMPLE 2

A compound of the formula 1 was prepared by the following method. The reaction procedure is represented later by the reaction formula 10.

(1) Preparation of Compound 6 in the Reaction Formula 10

Compound 2 (206 mg) prepared above in 47& aqueous HBr (6 ml) was stirred 1.5 hours, then allowed to cool and concentrated under reduced pressure. The resulting crude product was suspended in ethyl acetate (10 ml), and the resulting solid was recovered by filtration as the desired compound 6 in a yield of 215 mg.

Compound 6 showed the following NMR characteristics.

1H—NMR (500 MHz, DMSO-d6, δ ppm) 2.33–2.43 (m, 2H), 3.56 (t, J=6.0 Hz, 2H) 4.57 (t, J=7.5 Hz, 2H), 6.46 (s, 1H) 7.38 (d, J=9.0 Hz, 1H) 7.45 (s, 1H) 7.62 (dd, J=2.0 Hz, 9.0 Hz, 1H) 7.68–7.74 (m, 2H), 7.74–7.80 (m, 3H) 8.68 (d, J=9.5 Hz, 1H), 8.71 (d, J=9.5 Hz, 1H)

(2) Preparation of Compound 7 in the Reaction Formula 10

Compound 3 (15 mg) prepared above in DMF (0.7 ml) was stirred with N,N'-dimethyl-1,3-propanediamine (0.15 ml) at room temperature for 3 hours. After the reaction, the crude product was concentrated under reduced pressure made by a vacuum pump. Purification of the crude product by column chromatography (aminated silica gel NH-DM1020, product name, Fuji silycia Co. Ltd.; eluent chloroform/methanol=95/5) gave 12 mg of the desired compound 7.

Compound 7 showed the following NMR characteristics.

1H—NMR (500 MHz, DMSO-d6, δ ppm) 1.66–1.76 (m, 2H), 1.99–2.07 (m, 2H), 2.21 (s, 3H) 2.41 (t, J=6.5 Hz, 2H), 2.47 (s, 3H) 2.66 (t, J=7.0 Hz, 2H), 3.70 (s, 3H) 4.52 (t, J=6.5 Hz, 2H), 6.57 (d, J=12.5 Hz, 1H) 7.01–7.07 (m, 2H), 7.14 (t, J=7.5 Hz, 2H) 7.30 (t, J=7.5 Hz, 2H), 7.48–7.55 (m, 2H) 7.62 (d, J=7.0 Hz, 1H), 7.65–7.74 (m, 2H) 7.88 (t, J=13.0 Hz, 2H), 8.34 (d, J=8.0 Hz, 1H) 8.55 (d, J=6.5 Hz, 1H)

(3) Preparation of a Compound of the Formula 1 ("Compound 2" in the Reaction Formula 10)

Compound 7 (12 ml) in DMF (1 ml) was stirred with N-ethyldiisopropylamine (0.07 ml) and compound 6 (14 mg) at 70° C. for 2 hours and concentrated under reduced pressure made by a vacuum pump after the reaction.

Purification of the resulting crude product by column chromatography (aminated silica gel NH-DM1020, product name, Fuji silycia Co. Ltd.; eluent chloroform/methanol= 97/3) gave 4 mg of the desired compound of the formula 1.

The compound of the formula 1 ("compound 2" in the reaction formula 10) showed the following NMR characteristics.

1H—NMR (500 MHz, DMSO-d6, δ ppm) 1.30–1.40 (m, 2H), 1.88 (s, 3H), 1.91–2.01 (m, 4H) 2.07 (t, J=6.5 Hz, 2H), 2.11 (s, 3H) 2.14 (t, J=7.0 Hz, 2H), 2.28 (t, 2H) 2.33 (t, J=6.5 Hz, 2H), 4.31–4.38 (M,2H) 4.55 (t, 2H), 5.92 (s, 1H), 6.22 (d, J=2.5 Hz, 1H) 6.36 (s, 1H), 6.43 (d, J=12.0 Hz, 1H) 7.05 (d, J=13.5 Hz, 1H), 7.23–7.33 (m, 3H) 7.46–7.53 (m, 2H), 7.59 (d, J=8.0 Hz, 1H) 7.63–7.73 (m, 4H), 7.81 (t, J=8.5 Hz, 2H) 7.93 (t, J=9.0 Hz, 1H), 8.07 (d, J=9.0 Hz, 1H) 8.10 (d, J=13.0 Hz, 1H), 8.35 (d, J=7.0 Hz, 1H) 8.43 (d, J=8.0 Hz, 2H), 8.53 (d, J=9.0 Hz, 1H) 8.58 (d, J=9.5 Hz, 1H)

Reaction formula 10

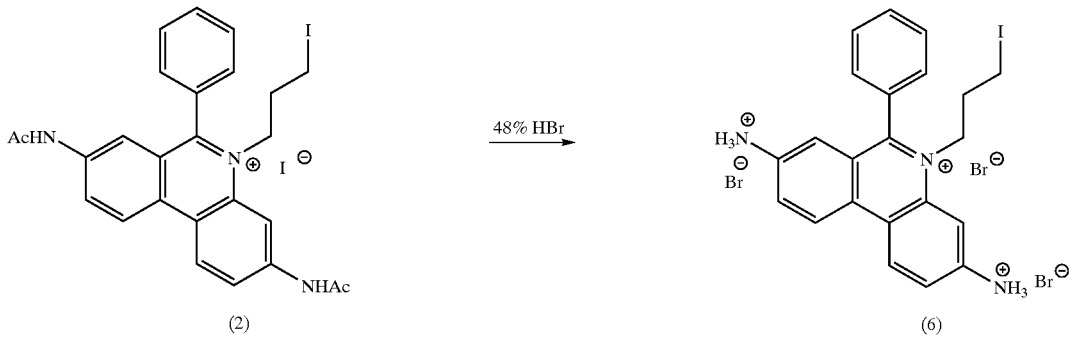

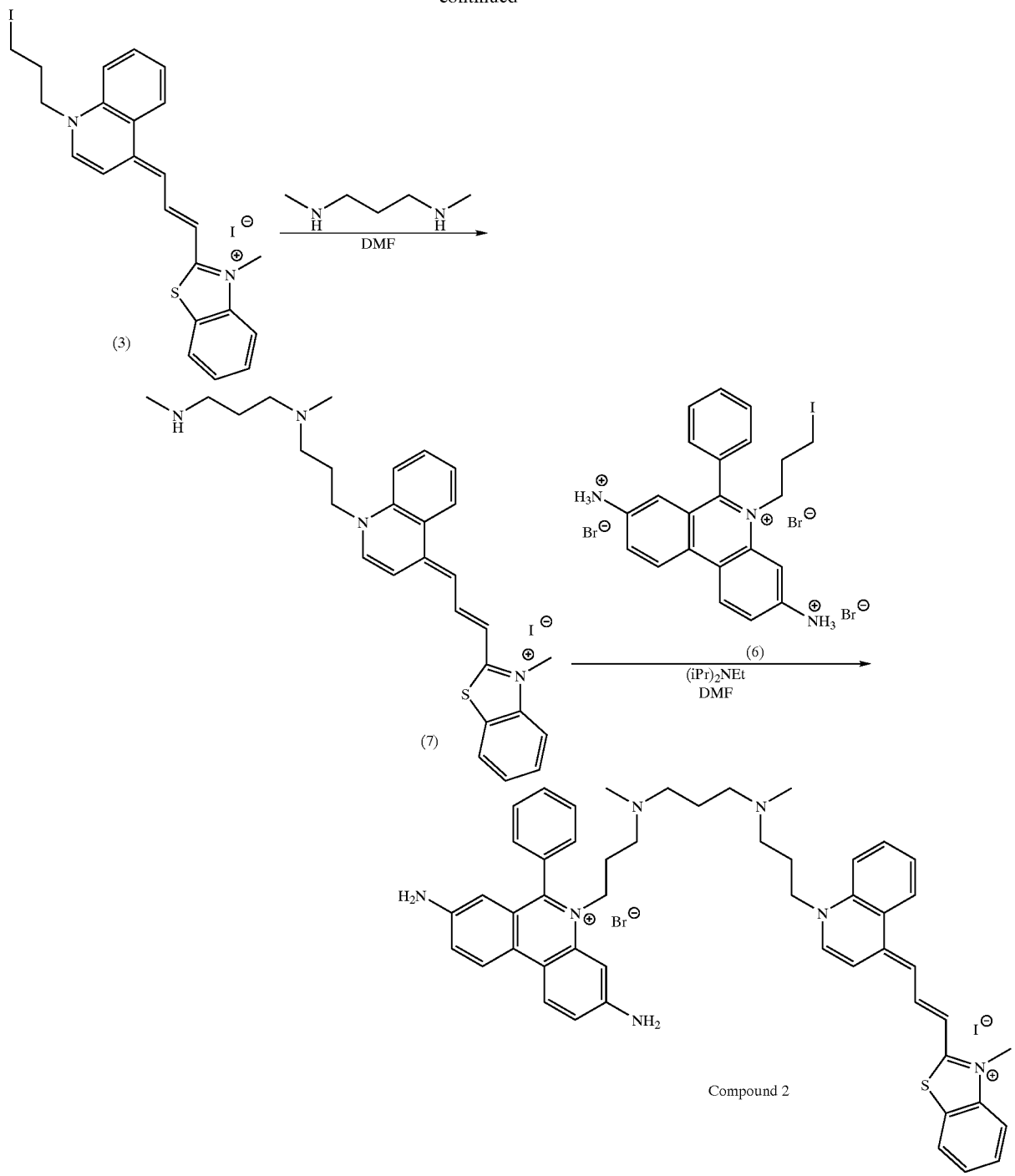

EXAMPLE 3

A compound of the formula 1 was prepared by the following method. The reaction procedure is represented later by the reaction formula 11.

(1) Preparation of Compound 8 in the Reaction Formula 11

Compound 6 (15 mg) obtained above in DMF (0.7 mg) was stirred with N,N'-dimethyl-1,3-propanediamine (0.15 ml) at room temperature for 3 hours. After the reaction, the crude product was concentrated under reduced pressure made by a vacuum pump. Purification of the crude product by column chromatography (aminated silica gel NH-DM1020, product name, Fuji silycia Co. Ltd.; eluent chloroform/methanol=9/1) gave 9 mg of the desired compound 8.

Compound 8 showed the following NMR characteristics.

1H—NMR (500 MHz, DMSO-d6, δ ppm) 1.38 (t, 2H), 1.85–2.00 (m, 5H), 2.10–2.18 (m, 2H) 2.20–2.38 (m, 7H), 4.40 (t, 2H), 5.94 (s, 1H) 6.27 (s, 1H), 6.41 (s, 1H), 7.28–7.36 (m, 2H) 7.51 (d, J=9.0 Hz, 1H), 7.65–7.78 (m, 3H) 8.59 (d, J=7.0 Hz, 1H), 8.64 (d, J=7.5 Hz, 1H)

(2) Preparation of a Compound of the Formula 1 ("Compound 2" in the Reaction Formula 11)

Compound 8 (9 mg) in DMF (1.2 ml) was stirred with compound 3 (10 mg) obtained above at 70° C. for 2 hours. After the reaction, the crude product 5 was concentrated under reduced pressure made by a vacuum pump. Purification of the crude product by column chromatography (aminated silica gel NH-DM1020, product name, Fuji silycia Co. Ltd.; eluent chloroform/methanol=97/3) gave 5 mg of the desired compound of the formula 1 ("compound 2" in the reaction formula 11).

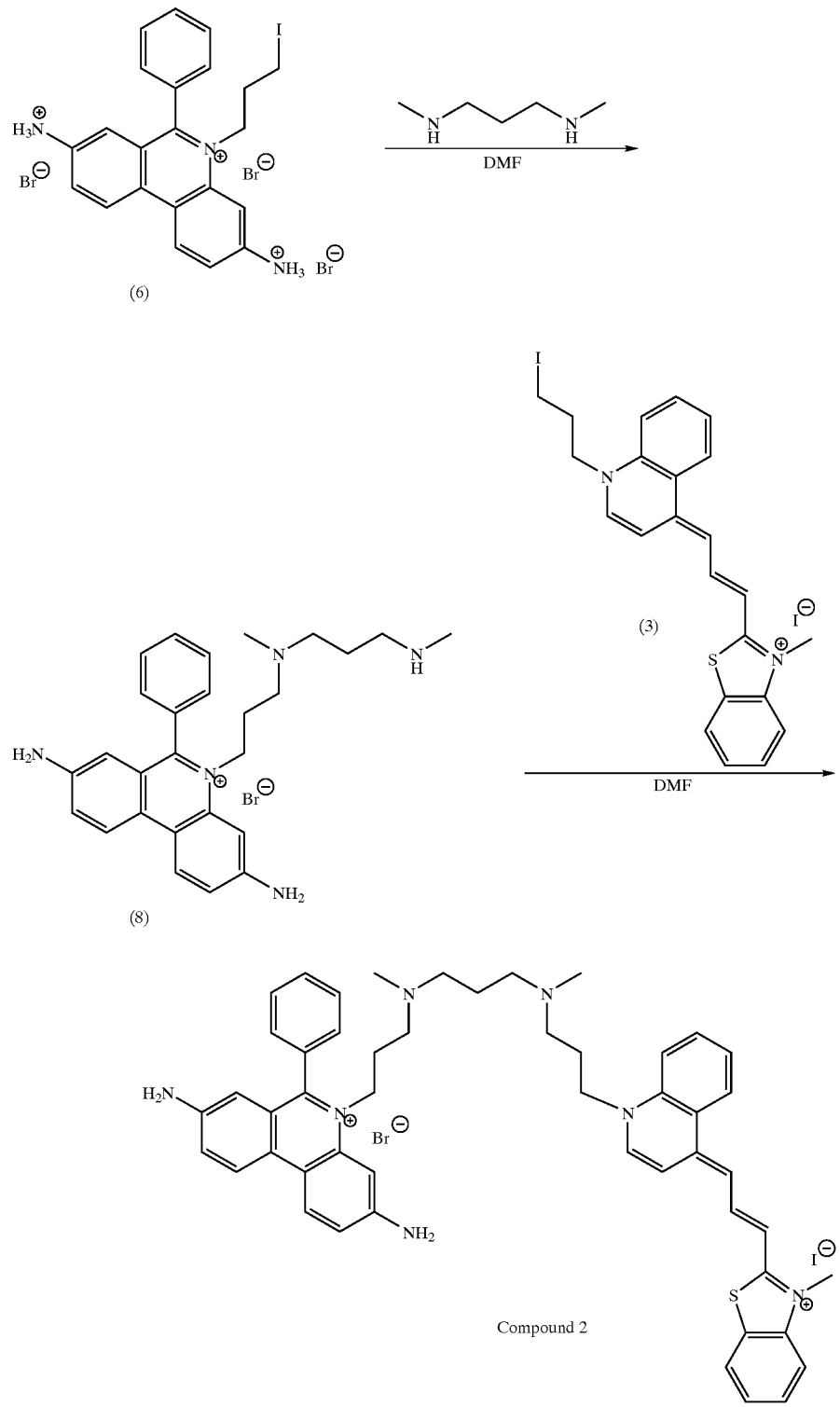

EXAMPLE 4

A compound of the formula 1 was prepared by the following method. The reaction procedure is represented later by the reaction formula 12.

(1) Preparation of Compound 10 in the Reaction Formula 12

N-methyl-1,3-propanediamine (2 g) and di-t-butyl dicarbonate (1.1 g) in methanol (16 ml) were stirred at room temperature for 1 hour. The resulting cured product was concentrated under reduced pressure and purified by silica gel column chromatography to give 140 mg of the desired compound 10.

Compound 10 showed the following NMR characteristics.

1H—NMR (500 MHz, DCD13, δ ppm) 1.44 (s, 9H), 1.70 (t, J=6.5 Hz, 2H), 2.44 (s, 3H) 2.66 (t, J=7.0 Hz, 2H), 3.17–3.24 (m, 2H) 3.17–3.24 (m, 2H), 3.42 (bs, 1H), 5.08 (bs, 1H)

(2) Preparation of Compound 11 in the Reaction Formula 12

Compound 10 (140 mg) thus obtained and compound 6 (40 mg) obtained above in DMF (1.8 ml) were stirred at room temperature for 3 hours. The resulting crude product was concentrated under reduced pressure and purified by column chromatography (aminated silica gel NH-DM1020, product name, Fuji silycia Co. Ltd.; eluent chloroform/methanol=95/5) to give 29 mg of the desired compound 11.

Compound 11 showed the following NMR characteristics.

$^1$H—NMR (500 MHz, DMSO-d6, δ ppm) 1.34–1.42 (m, 5H), 1.90 (s, 3H), 1.91–1.98 (m, 2H) 2.10 (t, J=7.0 Hz, 2H), 2.28 (t, J=6.0 Hz, 2H) 2.83 (t, J=7.0 Hz, 2H), 3.36 (bs, 1H) 4.37–4.45 (m, 2H), 5.93 (s, 1H), 6.27 (s, 1H) 6.40 (s, 1H), 7.30–7.38 (m, 2H) 7.52 (dd, J=2.5 Hz, 9.0 Hz, 1H), 7.65–7.80 (m, 3H) 8.59 (d, J=9.5 Hz, 1H), 8.65 (d, J=9.0 Hz, 1H)

(3) Preparation of Compound 12 in the Reaction Formula 12

Compound 11 (29 mg) thus obtained in methanol (2 ml) was stirred with 47% aqueous HBr (1 ml) at room temperature for 1 hour. The resulting crude product was concentrated under reduced pressure and purified by column chromatography (aminated silica gel NH-DM1020, product name, Fuji silycia Co. Ltd.; eluent chloroform/methanol= 95/5) to give 15 mg of the desired compound 12.

Compound 12 showed the following NMR characteristics.

1H—NMR (500 MHz, DMSO-d6, δ ppm) 1.29–1.40 (m, 2H), 1.80–2.01 (m, 4H) 2.13 (t, 2H), 2.22–2.35 (m, 5H) 4.35–4.48 (m, 2H), 5.94 (s, 1H), 6.26 (s, 1H) 6.43 (s, 1H), 7.26–7.35 (m, 2H) 7.48–7.52 (m, 1H), 7.68–7.80 (m, 3H) 8.57–8.67 (m, 2H)

(4) Preparation of a Compound of the Formula 1 ("compound 3" in the Reaction Formula 12)

Compound 12 (15 mg) and compound 3 (19 mg) obtained above in DMF (1.5 ml) were reacted at room temperature. After the reaction, the crude product was concentrated under reduced pressure and purified by column chromatography (aminated silica gel NH-DM1020, product name, Fuji silycia Co. Ltd.; eluent chloroform/methanol=95/5) to give 6 mg of the desired compound of the formula 1.

The compound of the formula 1 ("compound 3" in the reaction formula 12) showed the following NMR characteristics.

1H—NMR (500 MHz, DMSO-d6, δ ppm) 1.38 (t, J=7.0 Hz, 2H), 1.83–2.05 (m, 9H) 2.11 (t, 7.5 Hz, 2H), 2.24–2.33 (m, 2H) 2.36 (t, J=7.0 Hz, 2H), 3.72 (s, 3H) 4.31–4.41 (m, 2H), 4.60 (t, J=7.0 Hz, 2H) 5.94 (s, 1H), 6.23 (s, 1H), 6.38 (s, 1H) 6.46 (d, J=12.5 Hz, 1H), 7.09 (d, J=13.0 Hz, 1H) 7.24–7.36 (m, 3H), 7.44–7.54 (m, 2H) 7.56–7.77 (m, 7H) 7.80–7.86 (m, 1H) 7.92 (t, 1H), 8.06–8.14 (m, 1H) 8.38 (d, J=7.0 Hz, 1H), 8.45 (d, 1H) 8.56 (d, J=9.0 Hz, 1H), 8.61 (d, J=9.5 Hz, 1H)

Reaction formula 12

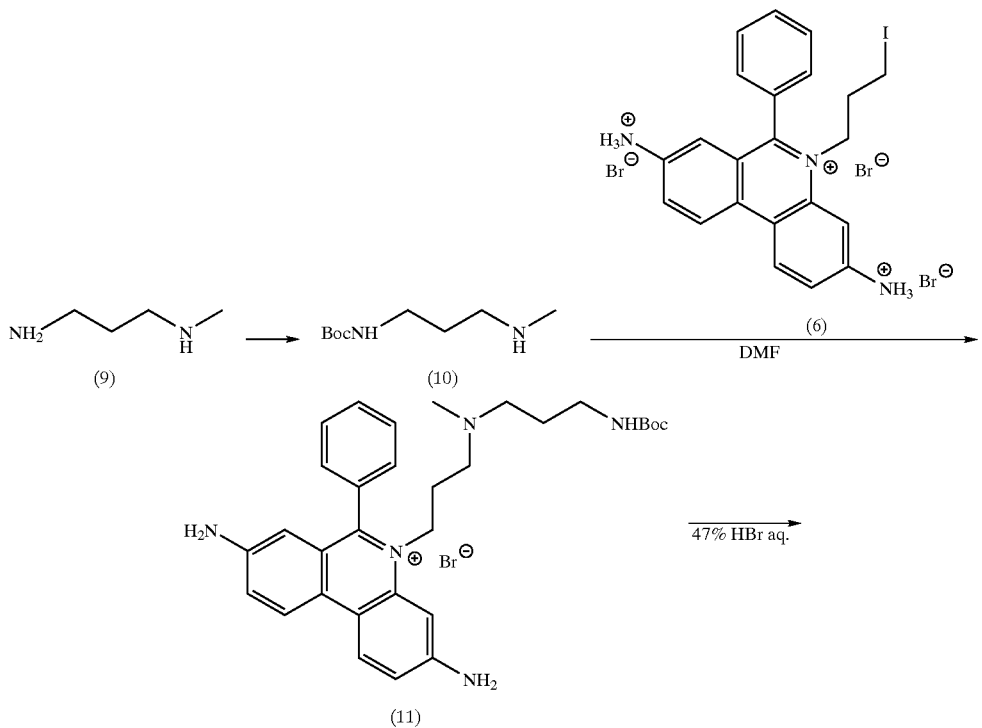

-continued

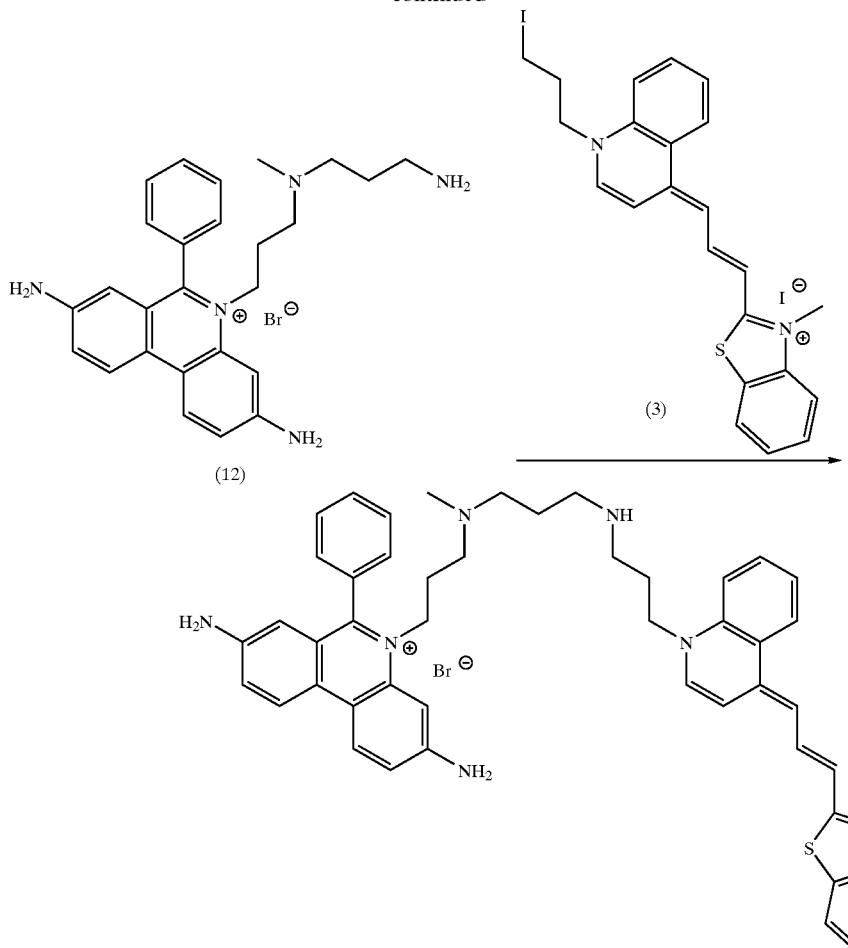

(3)

EXAMPLE 5

Detection of a Double-Stranded Nucleic Acid 1

Double-stranded nucleic acids were measured by using a compound of the formula 1 ("compound 1" in the reaction formula 9) prepared in Example 1. The double-stranded nucleic acids, dT30mer and dA30mer, having the nucleic acid sequences shown in SEQ ID NOS:1 and 2, respectively, were used.

0.3 nmol of a compound of the formula 1 ("compound 1" in the reaction formula 9) was dissolved in $H_2O$ (142.2 μl), and ×20 SSC (7.5 μl) and 0.5 M EDTA (0.3 μl) were added. The resulting solution was incubated at 75° C. for 30 minutes and allowed to cool to room temperature. The fluorescent intensity measured at room temperature at an excitation wavelength of 488 nm and an emission wavelength of 655 nm was 2.5.

Figure 1:
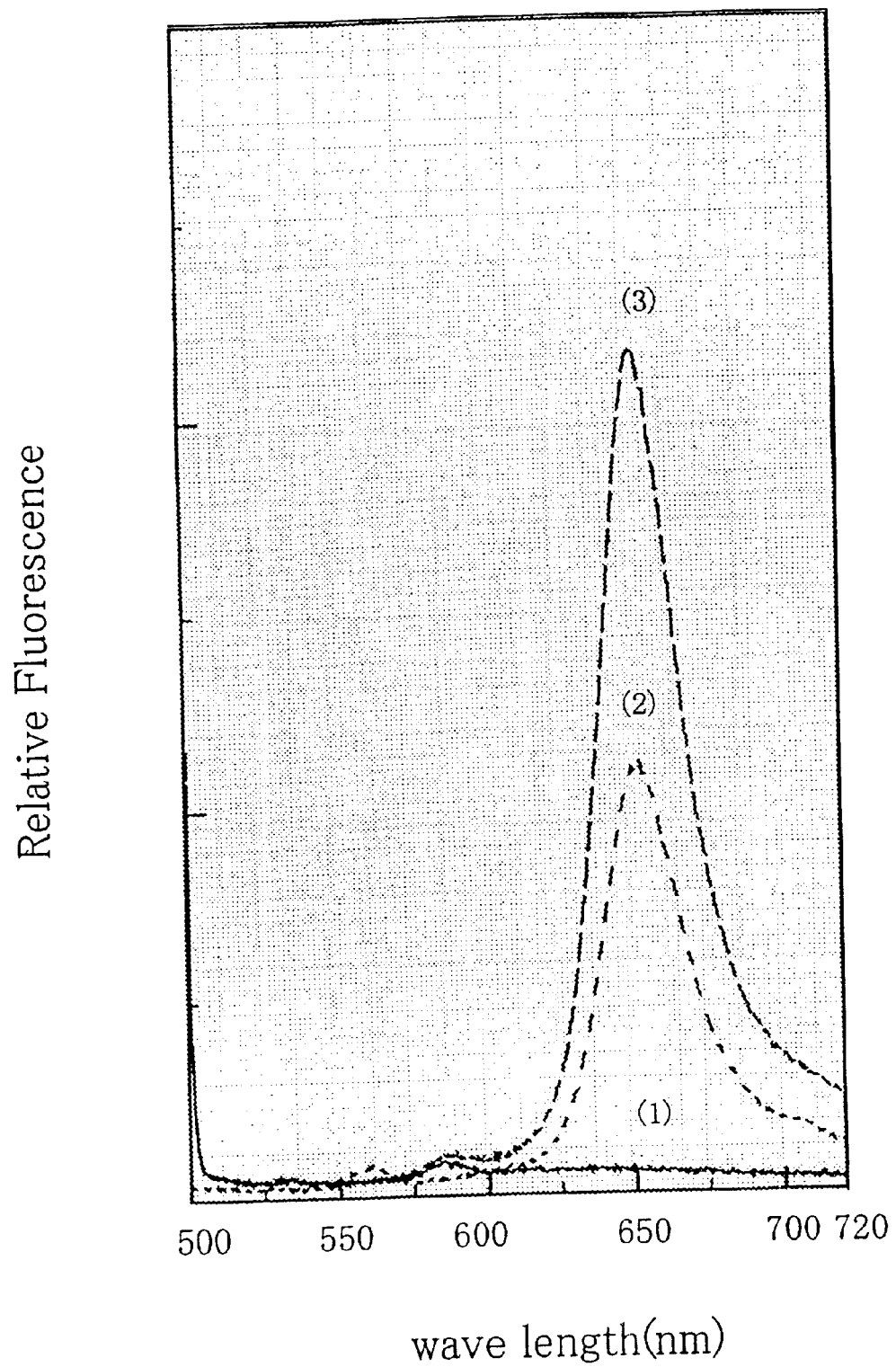
FIG. 1 shows the fluorescent spectra of compound 1 obtained in Example 5 (1) in the absence of a double-stranded nucleic acid at an excitation wavelength of 488 nm, (2) in the presence of dT30mer (0.04 nmol) and dA30mer (0.04 nmol) at an excitation wavelength of 470 nm, and (3)

Then, 0.3 nmol of the compound of the formula 1 ("compound 1" in the reaction formula 9), 0.04 nmol of dT30mer and 0.04 nmol of dA30mer were dissolved in $H_2O$ (142.2 μl), and ×20 SSC (7.5 μl) and 0.5 M EDTA (0.3 μl) were added. The resulting solution was incubated at 75° C. for 30 minutes and allowed to cool to room temperature. The fluorescent intensities measured at room temperature at an emission wavelength of 655 nm were 53.64 and 104.7, respectively, at excitation wavelengths of 470 nm and 488 nm, which indicates significant increase in fluorescent intensity in the presence of the double-stranded nucleic acids. The fluorescent spectrum obtained is shown in FIG. 1.

EXAMPLE 6

Detection of a Double-Stranded Nucleic Acid 2

Double-stranded nucleic acids were measured by using a compound of the formula 1 ("compound 2" in the reaction formula 10) prepared in Example 2. Double-stranded nucleic acids having the same nucleic acid sequences as in Example 5 were used.

0.3 nmol of a compound of the formula 1 ("compound 2" in the reaction formula 10) was dissolved in $H_2O$ (142.2 μl), and ×20 SSC (7.5 μl) and 0.5 M EDTA (0.3 μl) were added. The resulting solution was incubated at 75° C. for 30 minutes and allowed to cool to room temperature. The fluorescent intensity measured at room temperature at an excitation wavelength of 488 nm and an emission wavelength of 655 nm was 3.5.

Then, 0.3 nmol of the compound of the formula 1 ("compound 2" in the reaction formula 10), 0.04 nmol of dT30mer and 0.04 nmol of dA30mer were dissolved in $H_2O$ (142.2 μl), and ×20 SSC (7.5 μl) and 0.5 M EDTA (0.3 μl) were added. The resulting solution was incubated at 75° C.

for 30 minutes and allowed to cool to room temperature. The fluorescent intensities measured at room temperature at an emission wavelength of 655 nm were 53.64 and 104.7, respectively, at excitation wavelengths of 470 nm and 488 nm, which indicates significant increase in fluorescent intensity in the presence of the double-stranded nucleic acids. The fluorescent spectrum obtained is shown in FIG. 2.

EXAMPLE 7

A compound of the formula 1 was prepared by the following method. The reaction procedure is represented later by the reaction formula 13.

1. Preparation of Compound 13 in the Reaction Formula 13

A suspension of compound 1 (0.20 g) in the reaction formula 9 and 1, 6-diiodohexane (1.8 ml) were dissolved in nitrobenzene (1.8 ml) and stirred at 160° C. for 2.5 hours, then allowed to cool, and mixed with dichloromethane. The resulting solid was dissolved in hot methanol, mixed with ether, and allowed to stand at 0° C. The resulting solid was recovered by filtration as the desired compound 13a in a yield of 0.171 g.

$^1$H—NMR (500 MHz, DMSO-d6, δ ppm)

1.19 (m, 2H), 1.24 (m, 2H), 1.62 (m, 2H), 1.92 (m, 2H), 2.01 (s, 3H), 2.21 (s, 3H), 3.19 (t, 2H), 4.54 (m, 2H), 7.7–9.2 (m, 13H), 10.52 (s, 1H), 10.80 (s, 1H).

Similarly, 0.113 g of compound 13b and 0.139 g of compound 13c were prepared from compound 1 (0.10 g) and 1, 7-diiodoheptane (3 ml), and compound 1 (0.10 g) and 1, 8-diiodooctane (3 ml) respectively.

2. Preparation of Compound 14 in the Reaction Formula 13

A solution of compound 13a (117 mg) thus obtained and 3-aminopropanol (0.16 ml) were dissolved in DMF (3 ml) and stirred at 120° C. for 3 hours, then allowed to cool and concentrated under reduced pressure made by a vacuum pump. Purification of the crude product by silica gel column chromatography (eluent chloroform/methanol=90/10) gave 128 mg of the desired compound 14a.

$^1$H—NMR (500 MHz, DMSO-d6, δ ppm)

1.19 (m, 2H), 1.25 (m, 2H), 1.55 (m, 2H), 1.77 (m, 2H), 1.92 (m, 2H), 2.02 (s, 3H), 2.21 (s, 3H), 2.75–3.00 (m, 4H), 3.48 (m, 2H), 4.48 (m, 2H), 7.60–9.20 (m, 13H), 10.62 (s, 1H), 11.19 (s, 1H).

Similarly, 40 mg of compound 14b and 56 mg of compound 14c were prepared from compound 13b (0.113 g) and compound 13c (0.139 g), respectively.

3. Preparation of Compound 15 in the reaction formula 13

A solution of compound 14a (128 mg) thus obtained and 1 equivalent of compound 3 were dissolved in DMF (3 ml) and stirred at 130° C. for 2.5 hours, then allowed to cool and concentrated under reduced pressure made by a vacuum pump. Purification of the crude product by silica gel column chromatography (eluent ethyl acetate/acetic acid/water=60/30/20) gave 35 mg of the desired compound 14a.

Similarly, 7 mg of compound 15b and 8 mg of compound 15c were prepared from compound 14b (0.040 g) and compound 14c respectively.

4. Preparation of Compound 16 in the Reaction Formula 13

Compound 15a (35 mg) thus obtained was dissolved in 48% aqueous hydrobromic acid and stirred at 145° C. for 1 hour, and then allowed to cool and concentrated under reduced pressure. The resulting product was co-evaporated with ethanol to give a residue containing the desired product 16a (1.4 mg).

Similarly, 8 mg of a residue containing compound 16b and 8 mg of another residue containing compound 16c were prepared from compound 15b and compound 15c respectively.

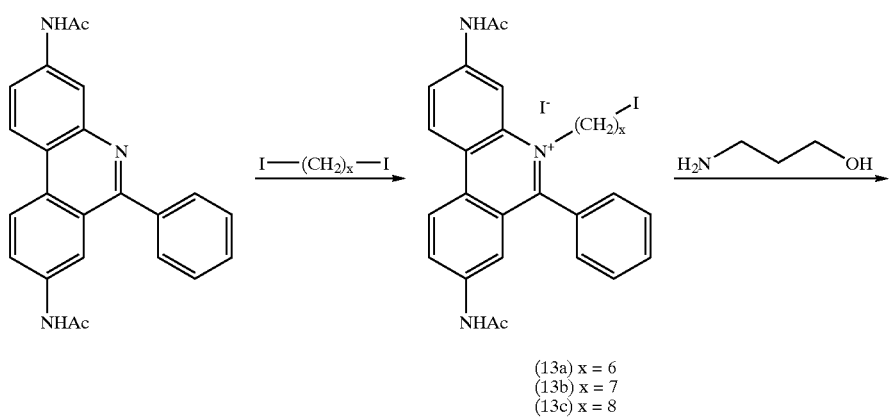

Reaction formula 13

(13a) x = 6
(13b) x = 7
(13c) x = 8

-continued
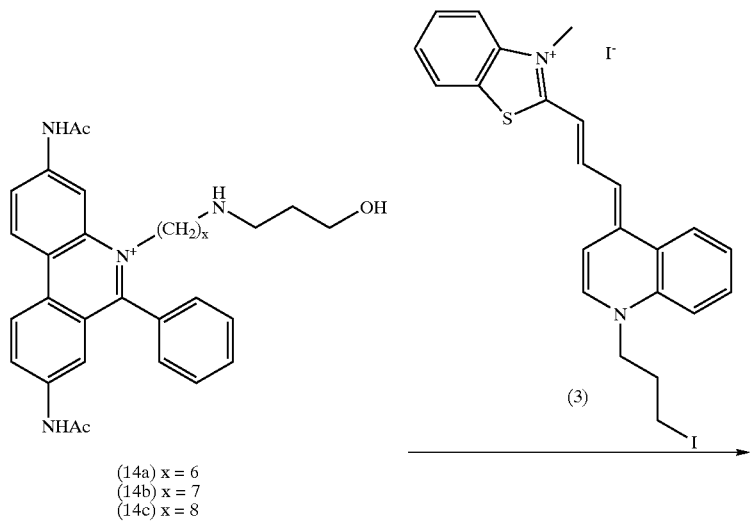
(14a) x = 6
(14b) x = 7
(14c) x = 8
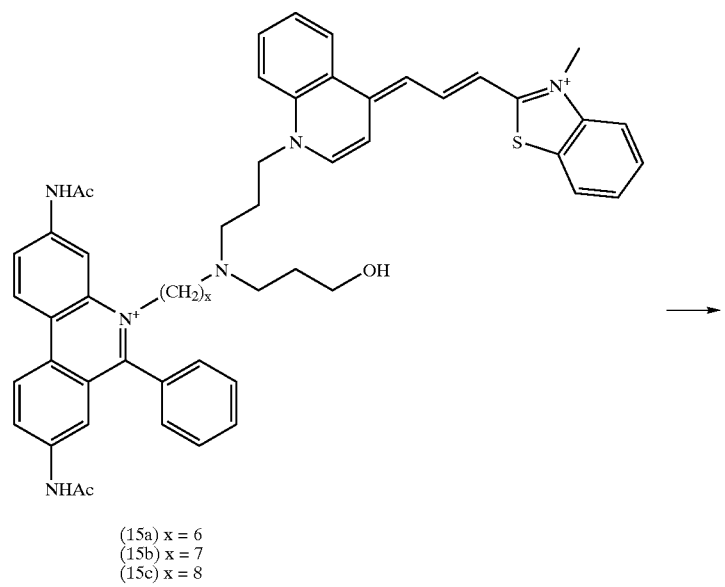
(15a) x = 6
(15b) x = 7
(15c) x = 8
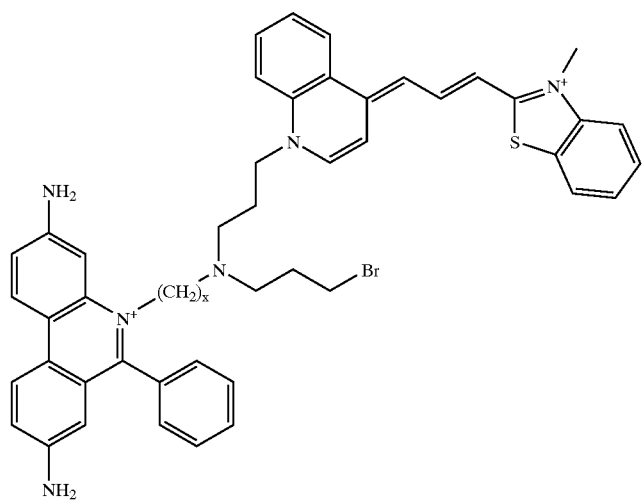
(16a) x = 6
(16b) x = 7
(16c) x = 8

EXAMPLE 8

A nucleic acid probe of the present invention was prepared by the following method. The reaction procedure is represented later by the reaction formula 14.

DNA oligomer (compound 17; 37 nmol) was dissolved in a mixed solution of distilled water (100 µl) and DMF (300 µl), and then mixed with dithiothreitol in DMF (1 M; 40 µl). After 1 hour, 133 µl of the reaction mixture was sampled, and then 100 µl of the solution of compound 16c (2 mg/ml) and 110 µl of triethylamine were added to the sampled reaction mixture. The mixture was allowed to stand at room temperature overnight, and then concentrated under reduced pressure made by a vacuum pump. The residue was extracted with n-butanol and water. The aqueous layer was mixed with butanol, mixed with ethanol, and allowed to stand at −78° C. for 30 minutes. The resulting precipitate was collected by centrifugation. The crude product was purified by HPLC (ODS-80Ts®, Tosoh) to give 0.94 nmol of the desired compound 18.

Reaction formula 14

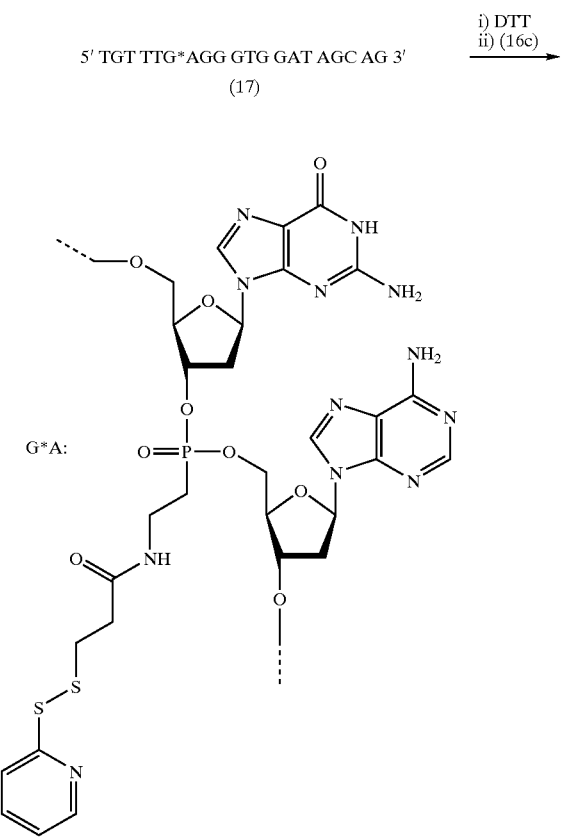

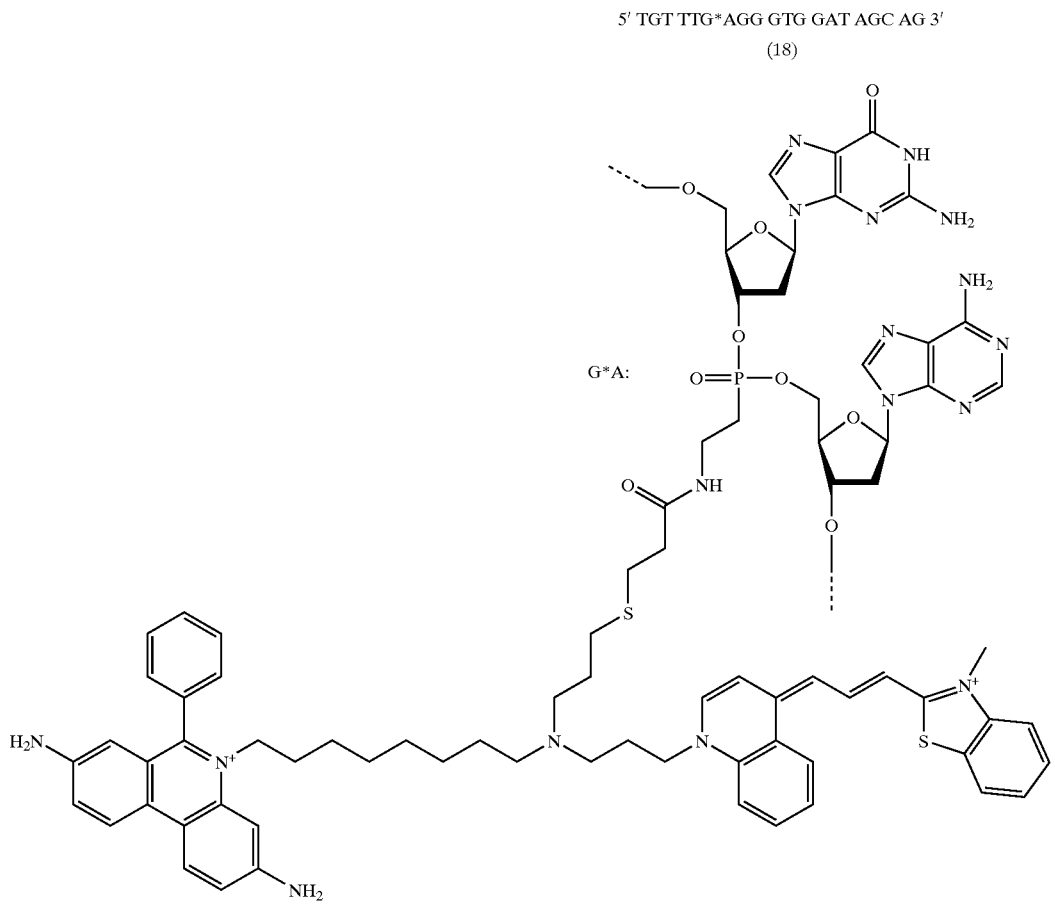

EXAMPLE 9

Double-stranded nucleic acids were measured by using the compound of the formula 1 ("compound 16c" in the reaction formula 13) prepared in Example 7. Double-stranded nucleic acids having the same nucleic acid sequences as in Example 5 were used.

(1) Double-stranded nucleic acids were measured by using the compound of the formula 1 ("compound 16c" in the reaction formula 13) prepared in Example 7. Double-stranded nucleic acids having the same nucleic acid sequences as in Example 5 were used. 30 µl of ×20 SSC, 1.2 µl of 0.5 M EDTA and 484.8 µl of distilled water were added to 60 µl of 25 µM solution of the compound of the formula 1 ("compound 16c" in the reaction formula 13).

(2) 144 µl of the reaction mixture of (1) was taken as a sample, and then 6 µl of TE buffer was added.

(3) 144 µl of the reaction mixture of (1) was taken as a sample, and then 3 µl of 12.5 µM solution of dT30mer and 3 µl of 12.5 µM solution of dA30mer were added.

(4) The mixture of (2) and the mixture of (3) were incubated at 75° C. for 30 minutes and allowed to cool to room temperature.

(5) The fluorescent intensities were measured at room temperature at an excitation wavelength of 470 nm.

The fluorescent intensity of the mixture of (2) measured at an emission wavelength of 654 nm was 5.79, and that of the mixture of (3) was 58.26. The results indicated significant increase in fluorescent intensity in the presence of the double-stranded nucleic acids. The fluorescent spectra obtained are shown in FIG. 3.

EXAMPLE 10

A target nucleic acid (DNA) was measured by using a nucleic acid probe of the present invention ("compound 18" in the reaction formula 14) prepared in Example 8. The nucleic acid sequence of the probe was shown in SEQ ID NO: 3 and the target nucleic acid was shown in SEQ ID NO: 4.

(1) 15.8 µl of ×20 SSC, 0.6 µl of 0.5 M EDTA and 260.8 µl of distilled water were added to 31.5 µl of 2.5 µM solution of a nucleic acid probe of the present invention ("compound 18" in the reaction formula 14).

(2) 147 µl of the reaction mixture of (1) was taken as a sample, and then 3 µl of TE buffer was added.

(3) 147 µl of the reaction mixture of (1) was taken as a sample, and then 3 µl of 50 µM solution of the target nucleic acid was added.

(4) The fluorescent intensities were measured at 41° C. at an excitation wavelength of 470 nm.

The fluorescent intensity of the mixture of (2) measured at an emission wavelength of 656 nm was 1.8, and that of the mixture of (3) was 5.7. The results indicated significant increase in fluorescent intensity in the presence of the target nucleic acids. The fluorescent spectra obtained are shown in FIG. 4.

As described above, according to the present invention, it is possible to provide a novel compound which is an unfamiliar fluorescent intercalative dye which shows a large fluorescent enhancement upon intercalation into a double-stranded nucleic acid when used in detection of the nucleic acid, and shows a great difference between the excitation wavelength and the emission wavelength (i.e., has a large Stokes shift). The compound is used for conventional nucleic acid assay by contacting it with a double-stranded nucleic acid or by linking it with a single-stranded oligonucleotide to from a nucleic acid probe.

Especially, a nucleic acid probe obtained by linking the compound of the present invention with a single-stranded oligonucleotide via an appropriate linker enhances its fluorescence only when the single-stranded oligonucleotide is hybridized with a nucleic acid having a specific sequence and therefore enables simple and one-step homogeneous assay of a nucleic acid without separation of the unhybridized probe.

The compound of the present invention is characterized in that its fluorescent spectrum does not overlap with that of any known fluorescent intercalative dye. Therefore, combined use of at least two nucleic acid probes using the compound of the present invention and conventionally known fluorescent intercalative dye(s) makes it possible to measure the amplification products from at least two target nucleic acids in a sample in a closed vessel without separation while amplifying the target nucleic acids, i.e., measure at least target nucleic acids simultaneously.

What is claimed is:

1. A compound represented by formula 1 or a salt, hydrate, solvate or stereoisomer thereof:

Formula 1

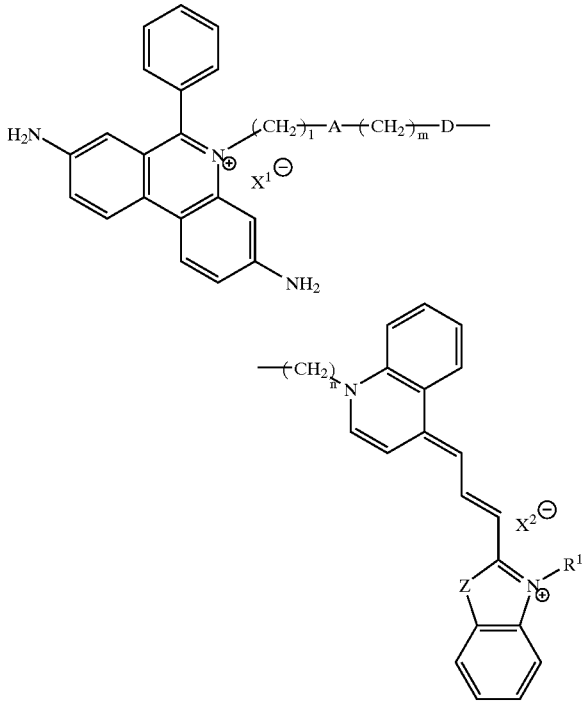

wherein
R¹ is a lower alkyl group,
A and D, which may be the same or different, each is a group represented by the formula —CHR²— (wherein R² is a hydrogen atom, a lower alkyl group or a lower alkyl group substituted with a halogen atom), a group represented by the formula —NR³— (wherein R³ is a hydrogen atom, a lower alkyl group or a lower alkyl group substituted with a halogen atom), a group represented by the formula —N⁺R⁴R⁵·Q⁻— (wherein each of R⁴ and R⁵, which may be the same or different, is a lower alkyl group or a lower alkyl group substituted with a halogen atom, and Q is a halogen atom, a group represented by the formula R⁶COO (wherein R⁶ is a lower alkyl group or a lower alkyl group substituted with a halogen atom) or a group represented by the formula R⁷SO₃ (wherein R⁷ is a lower alkyl group, a lower alkyl group substituted with a halogen atom or a phenyl group which may be substituted with a lower alkyl group)), an oxygen atom or a sulfur atom, each of
l, m and n, which may be the same or different, is an integer of from 2 to 5,
Z is an oxygen atom or a sulfur atom, and each of
X¹ and X², which may be the same or different, is a halogen atom, a group represented by the formula R⁸COO (wherein R⁸ is a lower alkyl group or a lower alkyl group substituted with a halogen atom) or a group represented by the formula R⁹SO₃ (wherein R⁹ a lower alkyl group, a lower alkyl group substituted with a halogen atom or a phenyl group which may be substituted with a lower alkyl group).

2. A nucleic acid probe comprising a single-stranded oligonucleotide having a sequence complementary to a specific sequence in a nucleic acid (target nucleic acid) containing the specific sequence and a compound represented by formula 1 linked to the single-stranded oligonucleotide by a chemical bond.

3. The nucleic acid probe according to claim wherein the single-stranded oligonucleotide is a DNA oligomer.

4. The nucleic acid probe according to claim 3, wherein a phosphorus atom in the DNA oligomer is linked by the chemical bond via a linker.

5. The nucleic acid probe according to claim 4, wherein the compound represented by the formula 1 alters its fluorescent characteristics upon intercalation into the double strand resulting from hybridization of the target nucleic acid and the single-stranded DNA probe.

6. A method of measuring at least one nucleic acid (target nucleic acid) containing a specific nucleic acid sequence in a sample, which uses the nucleic acid probe as defined in claim 3.

7. A method of measuring at least two RNAs (target RNAs) having specific nucleic acid sequences in a sample, which comprises
amplifying the target RNAs simultaneously in the presence of probes which are complementary to the respective amplification products and labeled with different fluorescent intercalative dyes, and
measuring the change in fluorescence intensity resulting from intercalation into the double strands formed by hybridization of the amplification products and the probes,
wherein one of the fluorescent intercalative dyes is the compound represented by formula 1, and the other is a fluorescent intercalative dye which is excited by a radiation at the same wavelength as the compound represented by the formula 1 but emits fluorescence at a wavelength different from the wavelength of the fluorescence from the compound represented by the formula 1.

8. A method of measuring at least one RNA (target RNA) having a specific nucleic acid sequence in a sample, comprising:
amplifying the target RNA and a known amount of a standard nucleic acid added to the sample simultaneously in the presence of probes which are complementary to the respective amplification products and labeled with different fluorescent intercalative dyes, measuring the fluorescence intensity which has changed due to intercalation of the fluorescent intercalative dyes into the double strands formed by hybridization of the amplification products and the probes, and
comparing the fluorescence intensity with that measured in the presence of a known amount of the standard nucleic acid, wherein one of the fluorescent intercalative dyes is the compound represented by formula 1, and the other is a fluorescent intercalative dye which is excited by a radiation at the same wavelength as the compound represented by the formula 1 but emits fluorescence at a wavelength different from the wavelength of the fluorescence from the compound represented by the formula 1.

9. The method according to claim 7 or 8, wherein the other fluorescent intercalative dye is oxazole yellow.

10. The method according to claim 9, wherein the excitation wavelengths of the fluorescent intercalative dyes are from 450 nm to 500 nm.

11. A method of detecting or quantifying a nucleic acid anticipated to be contained in a sample, which comprises:

mixing the compound of claim 1 with a test sample anticipated to contain a double-stranded nucleic acid and measuring the fluorescence intensity of the sample.

12. A method of detecting or quantifying a nucleic acid anticipated to be contained in a sample, which comprises:

mixing the compound of claim 1 with a test sample anticipated to contain a double-stranded nucleic acid, measuring the fluorescence intensity of the sample and comparing the fluorescence intensity of said test sample with the fluorescence intensity of a sample containing a known amount of the double-stranded nucleic acid mixed with the compound of claim 1.

13. The method of claim 11, wherein the double-stranded nucleic acid is double-stranded DNA, double stranded RNA or a DNA/RNA hybrid.

14. A method of producing the compound of claim 1, or a salt, hydrate, solvate or stereoisomer thereof, comprising:

performing the reaction described by reaction formula 1:

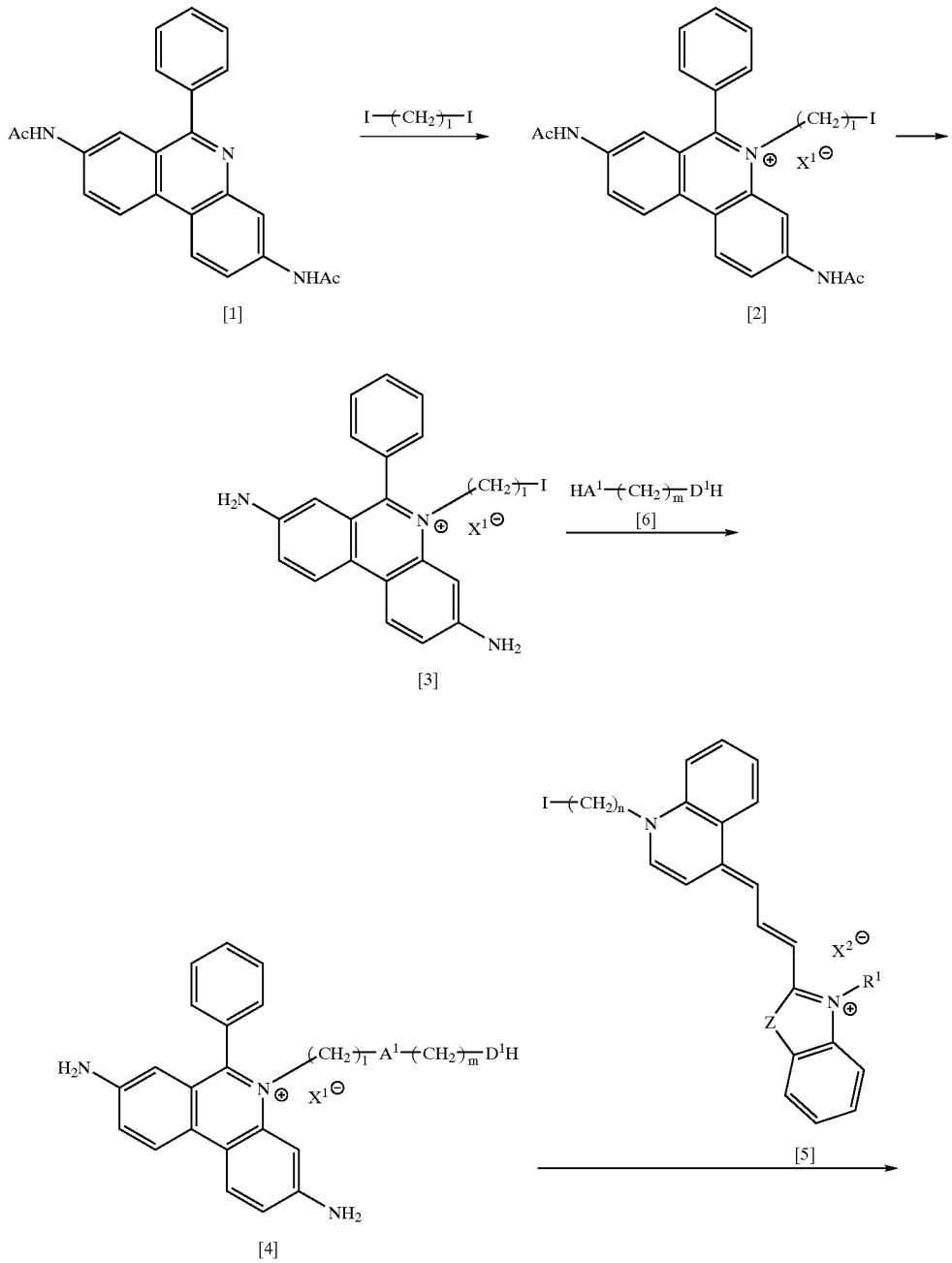

-continued

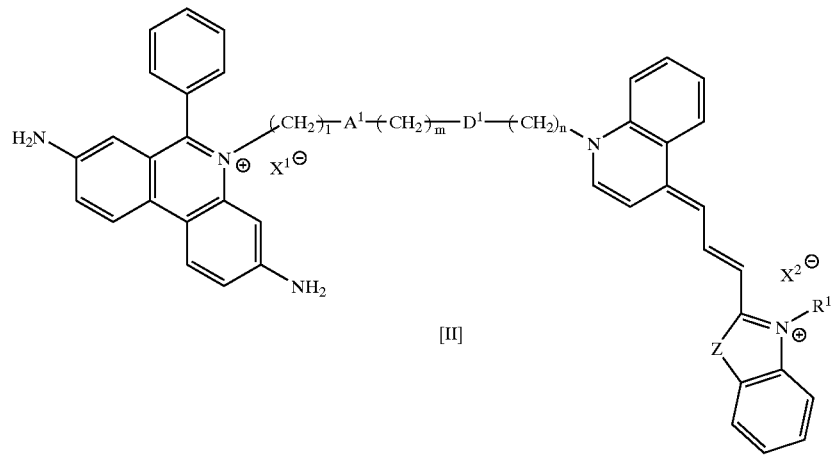

[II]

wherein
R¹ is a lower alkyl group;
A¹ and D¹, which may be the same or different, each is a group represented by the formula —NR³— (wherein R³ is a hydrogen atom, a lower alkyl group or a lower alkyl group substituted with a halogen atom), a group represented by the formula —N⁺R⁴R⁵·Q⁻— (wherein each of R⁴ and R⁵, which may be the same or different, is a lower alkyl group or a lower alkyl group substituted with a halogen atom, and Q is a halogen atom, a group represented by the formula R⁶COO (wherein R⁶ a lower alkyl group or a lower alkyl group substituted with a halogen atom) or a group represented by the formula R⁷SO₃ (wherein R⁷ a lower alkyl group, a lower alkyl group substituted with a halogen atom or a phenyl group which may be substituted with a lower alkyl group)), an oxygen atom or a sulfur atom;
l, m and n, which may be the same or different, each is an integer of from 2 to 5;
Z is an oxygen atom or a sulfur atom; and
X¹ and X², which may be the same or different, each is a halogen atom, a group represented by the formula R⁸COO (wherein R⁸ is a lower alkyl group or a lower alkyl group substituted with a halogen atom) or a group represented by the formula R⁹SO₃ (wherein R⁹ a lower alkyl group, a lower alkyl group substituted with a halogen atom or a phenyl group which may be substituted with a lower alkyl group).

15. A method of producing the compound of claim 1, or a salt, hydrate, solvate or stereoisomer thereof, comprising:
performing the reaction described by reaction formula 2:

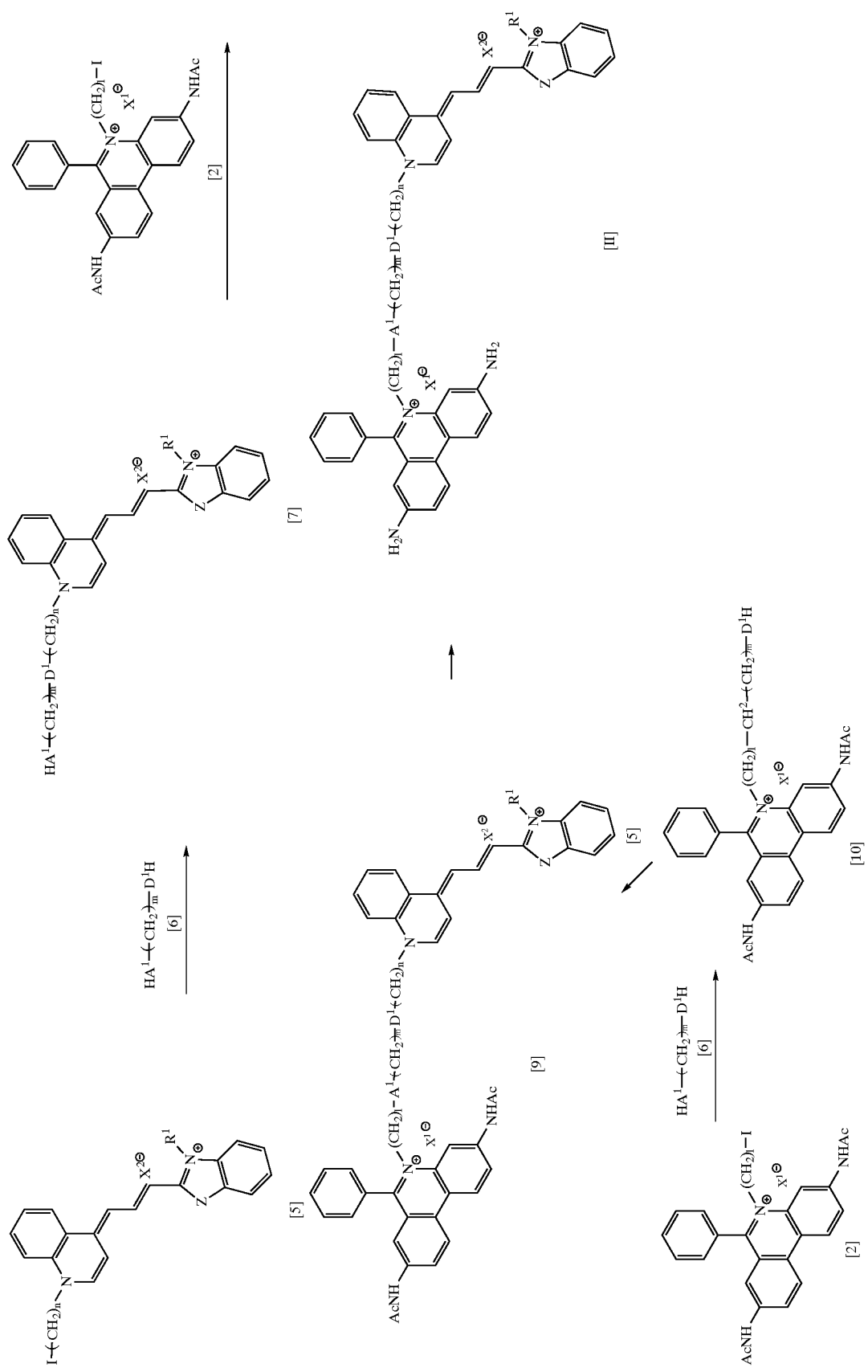

wherein
R¹ is a lower alkyl group;
A¹ and D¹, which may be the same or different, each is a group represented by the formula —NR³— (wherein R³ is a hydrogen atom, a lower alkyl group or a lower alkyl group substituted with a halogen atom), a group represented by the formula —N⁺R⁴R⁵·Q⁻— (wherein each of R⁴ and R⁵, which may be the same or different, is a lower alkyl group or a lower alkyl group substituted with a halogen atom, and Q is a halogen atom, a group represented by the formula R⁶COO (wherein R⁶ is a lower alkyl group or a lower alkyl group substituted with a halogen atom) or a group represented by the formula R⁷SO₃ (wherein R⁷ is a lower alkyl group, a lower alkyl group substituted with a halogen atom or a phenyl group which may be substituted with a lower alkyl group)), an oxygen atom or a sulfur atom;
1, m and n, which may be the same or different, each is an integer of from 2 to 5;
Z is an oxygen atom or a sulfur atom; and
X¹ and X², which may be the same or different, each is a halogen atom, a group represented by the formula R⁸COO (wherein R⁸ is a lower alkyl group or a lower alkyl group substituted with a halogen atom) or a group represented by the formula R⁹SO₃ (wherein R⁹ a lower alkyl group, a lower alkyl group substituted with a halogen atom or a phenyl group which may be substituted with a lower alkyl group).

16. A method of producing the compound of claim 1, or a salt, hydrate, solvate or stereoisomer thereof, comprising: performing the reaction described by reaction formula 3:

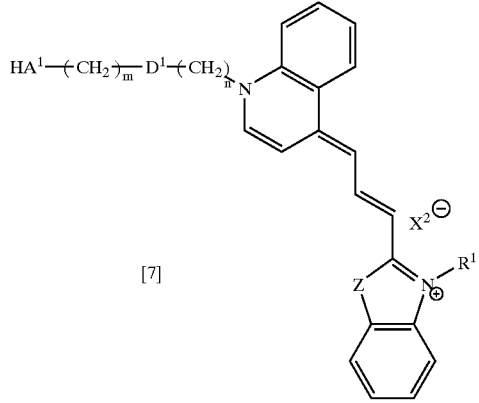
[7]

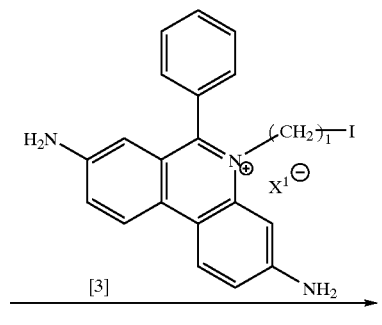
[3]

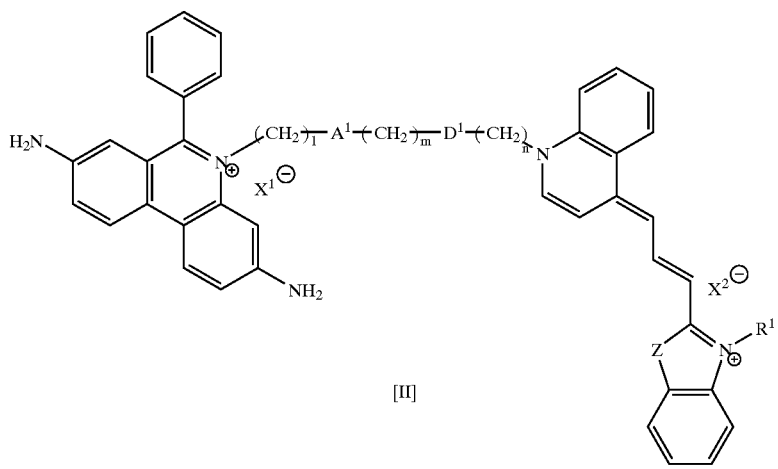
[II]

wherein
R¹ is a lower alkyl group;
A¹ and D¹, which may be the same or different, each is a group represented by the formula —NR³— (wherein R³ is a hydrogen atom, a lower alkyl group or a lower alkyl group substituted with a halogen atom), a group represented by the formula —N⁺R⁴R⁵·Q⁻— (wherein each of R⁴ and R⁵, which may be the same or different, is a lower alkyl group or a lower alkyl group substituted with a halogen atom, and Q is a halogen atom, a group represented by the formula R⁶COO (wherein R⁶ is a lower alkyl group or a lower alkyl group substituted with a halogen atom) or a group represented by the formula R⁷SO₃ (wherein R⁷ is a lower alkyl group, a lower alkyl group substituted with a halogen atom or a phenyl group which may be substituted with a lower alkyl group)), an oxygen atom or a sulfur atom;

l, m and n, which may be the same or different, each is an integer of from 2 to 5;

Z is an oxygen atom or a sulfur atom; and

X¹ and X², which may be the same or different, each is a halogen atom, a group represented by the formula R⁸COO (wherein R⁸ is a lower alkyl group or a lower alkyl group substituted with a halogen atom) or a group represented by the formula R⁹SO₃ (wherein R⁹ a lower alkyl group, a lower alkyl group substituted with a halogen atom or a phenyl group which may be substituted with a lower alkyl group).

17. A method of producing the compound of claim 1, or a salt, hydrate, solvate or stereoisomer thereof, comprising: performing the reaction described by reaction formula 4:

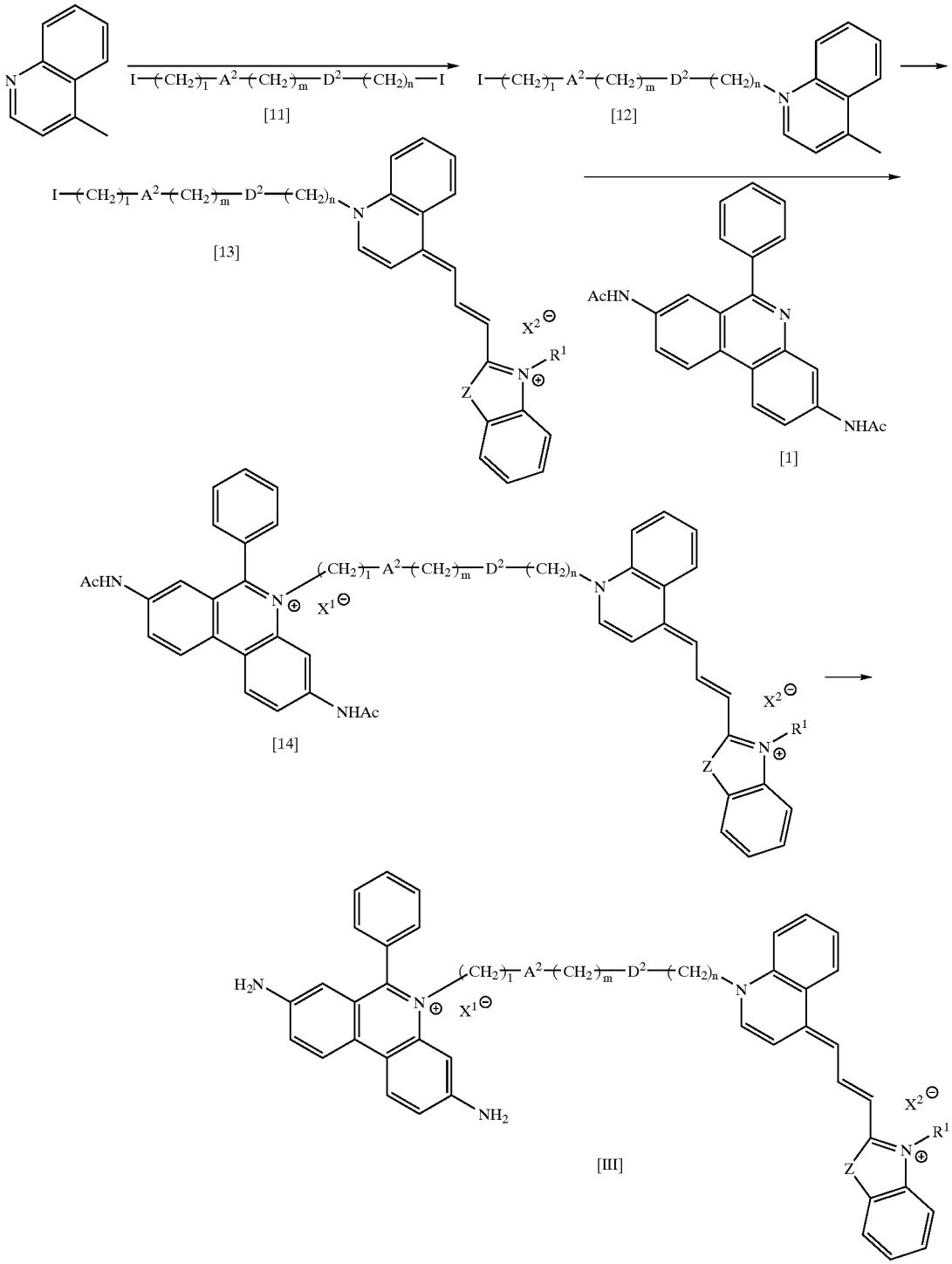

wherein
- R$^1$ is a lower alkyl group;
- A$^2$ and D$^2$, which may be the same or different, each is a group represented by the formula —CHR$^2$— (wherein R$^2$ is a hydrogen atom, a lower alkyl group or a lower alkyl group substituted with a halogen atom), an oxygen atom or a sulfur atom;
- l, m, and n, which may be the same or different, each is an integer of from 2 to 5;
- Z is an oxygen atom or a sulfur atom; and
- X$^1$ and X$^2$, which may be the same or different, each is a halogen atom, a group represented by the formula R$^8$COO (wherein R$^8$ is a lower alkyl group or a lower alkyl group substituted with a halogen atom) or a group represented by the formula R$^9$SO$_3$ (wherein R$^9$ a lower alkyl group, a lower alkyl group substituted with a halogen atom or a phenyl group which may be substituted with a lower alkyl group).

18. A method of producing the compound of claim 1, or a salt, hydrate, solvate or stereoisomer thereof, comprising: performing the reaction described by reaction formula 5:

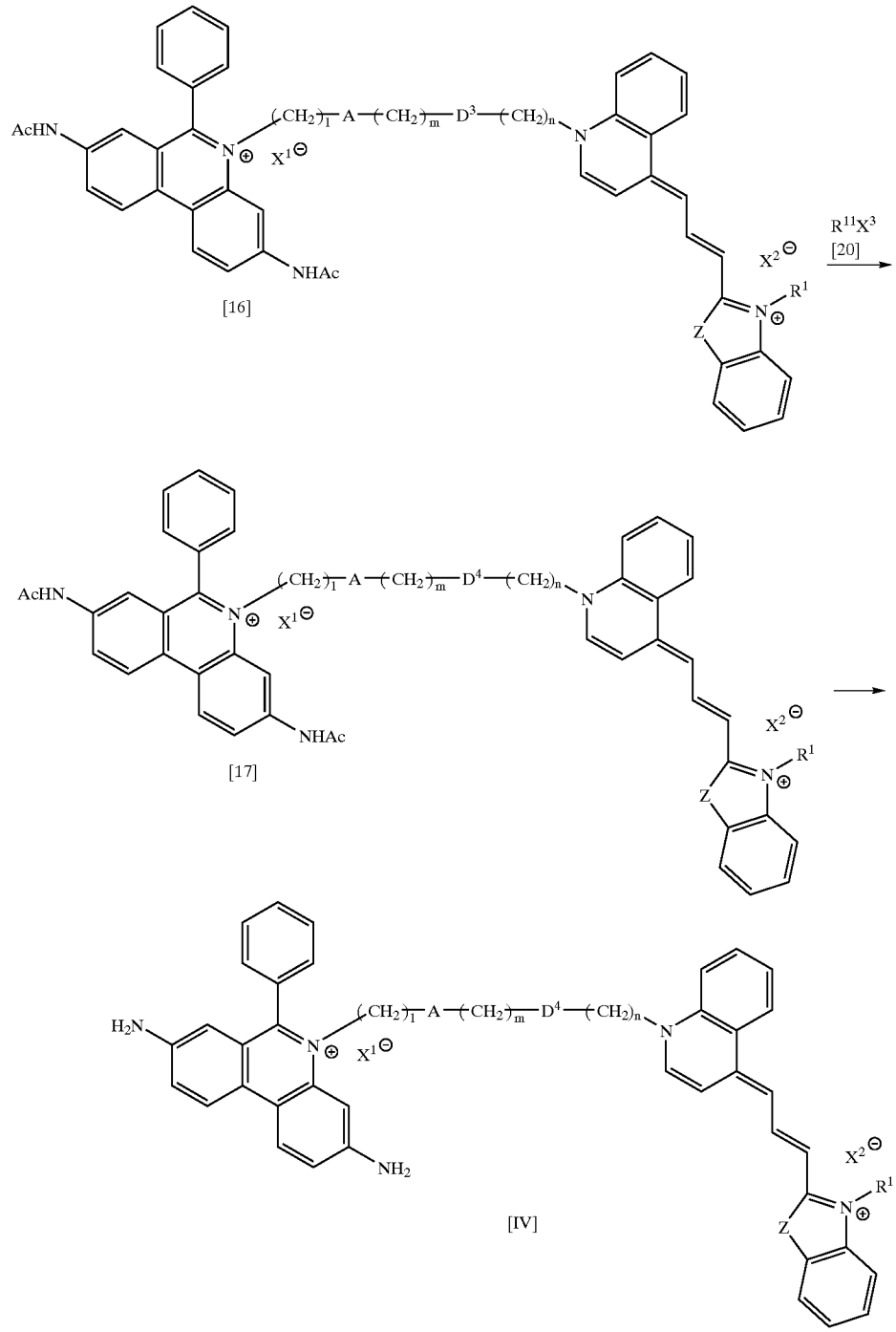

wherein
- $R^1$ is a lower alkyl group;
- A is a group represented by the formula —$CHR^2$— (wherein $R^2$ is a hydrogen atom, a lower alkyl group or a lower alkyl group substituted with a halogen atom), a group represented by the formula —$NR^3$— (wherein $R^3$ is a hydrogen atom, a lower alkyl group or a lower alkyl group substituted with a halogen atom), a group represented by the formula —$N^+R^4R^5 \cdot Q^-$— (wherein each of $R^4$ and $R^5$, which may be the same or different, is a lower alkyl group or a lower alkyl group substituted with a halogen atom, and Q is a halogen atom, a group represented by the formula $R^6COO$ (wherein $R^6$ a lower alkyl group or a lower alkyl group substituted with a halogen atom) or a group represented by the formula $R^7SO_3$ (wherein $R^7$ is a lower alkyl group, a lower alkyl group substituted with a halogen atom or a phenyl group which may be substituted with a lower alkyl group)), an oxygen atom or a sulfur atom;
- $D^3$ is a group represented by the formula —$NR^3$— (wherein $R^3$ is a hydrogen atom, a lower alkyl group or a lower alkyl group substituted by a halogen atom);
- $D^4$ is a group represented by —$NR^{10}$— (wherein $R^{10}$ is a hydrogen atom, a lower alkyl group, or a lower alkyl group substituted with a halogen atom), a group represented by the formula —$N^+R^4R^5 \cdot Q^-$— (wherein each of $R^4$ and $R^5$, which may be the same or different, is a lower alkyl group or a lower alkyl group substituted with a halogen atom, and Q is a halogen atom, a group represented by the formula $R^6COO$ (wherein $R^6$ is a lower alkyl group or a lower alkyl group substituted with a halogen atom) or a group represented by the formula $R^7SO_3$ (wherein $R^7$ is a lower alkyl group, a lower alkyl group substituted with a halogen atom or a phenyl group which may be substituted with a lower alkyl group);
- 1, m and n, which may be the same or different, is an integer of from 2 to 5;
- Z is an oxygen atom or a sulfur atom;
- $X^1$ and $X^2$, which may be the same or different, each is a halogen atom, a group represented by the formula $R^8COO$ (wherein $R^8$ is a lower alkyl group or a lower alkyl group substituted with a halogen atom) or a group represented by the formula $R^9SO_3$ (wherein $R^9$ is a lower alkyl group, a lower alkyl group substituted with a halogen atom or a phenyl group which may be substituted with a lower alkyl group);
- $X^3$ is a halogen atom, or a group represented by the formula $R^9SO_3$ (wherein $R^9$ is a lower alkyl group, a lower alkyl group substituted with a halogen atom or a phenyl group which may be substituted with a lower alkyl group); and
- $R^{11}$ is a lower alkyl group or a lower alkyl group substituted with a halogen atom.

19. A method of producing the compound of claim 1, or a salt, hydrate, solvate or stereoisomer thereof, comprising:
performing the reaction described by reaction formula 6:

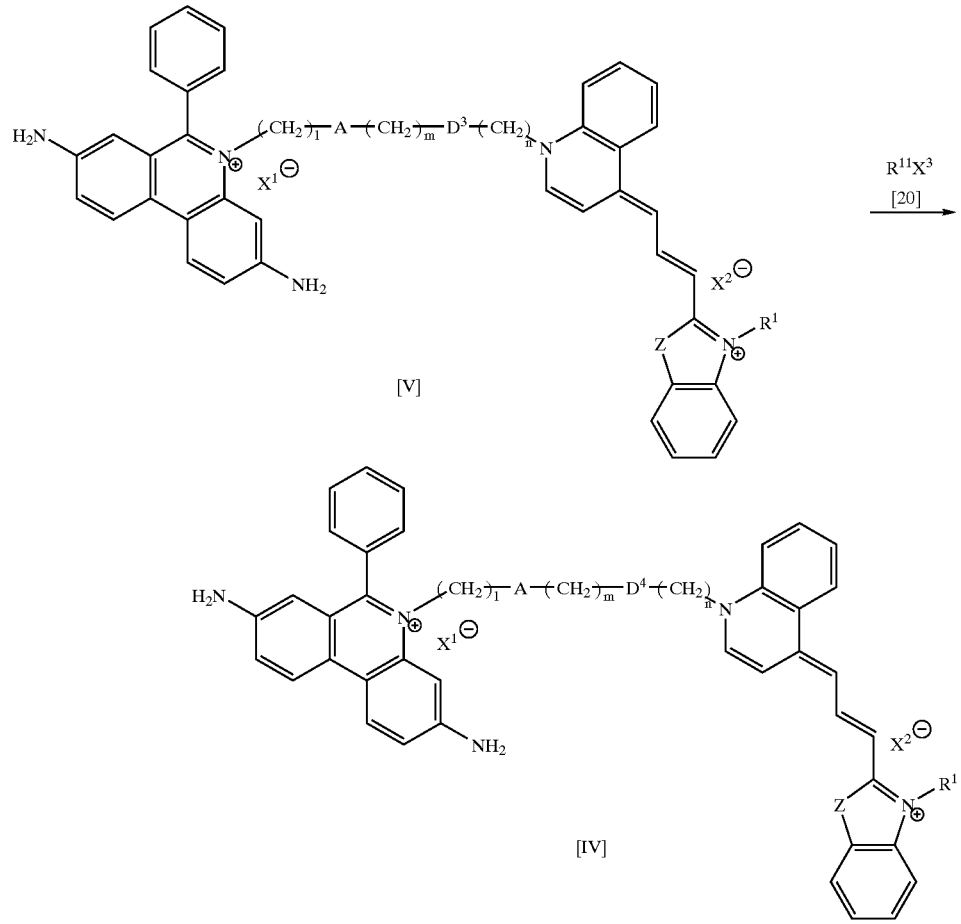

wherein

R¹ is a lower alkyl group;

A is a group represented by the formula —CHR² —(wherein R² is a hydrogen atom, a lower alkyl group or a lower alkyl group substituted with a halogen atom), a group represented by the formula —NR³ —(wherein R³ is a hydrogen atom, a lower alkyl group or a lower alkyl group substituted with a halogen atom), a group represented by the formula —N⁺R⁴R⁵·Q⁻— (wherein each of R⁴ and R⁵, which may be the same or different, is a lower alkyl group or a lower alkyl group substituted with a halogen atom, and Q is a halogen atom, a group represented by the formula R⁶COO (wherein R⁶ is a lower alkyl group or a lower alkyl group substituted with a halogen atom) or a group represented by the formula R⁷SO₃ (wherein R⁷ a lower alkyl group, a lower alkyl group substituted with a halogen atom or a phenyl group which may be substituted with a lower alkyl group)), an oxygen atom or a sulfur atom;

l, m and n, which may be the same or different, each is an integer of from 2 to 5;

Z is an oxygen atom or a sulfur atom;

D³ is a group represented by the formula —NR³ —(wherein R³ is a hydrogen atom, a lower alkyl group or a lower alkyl group substituted by a halogen atom);

D⁴ is a group represented by —NR¹⁰ —(wherein R¹⁰ is a hydrogen atom, a lower alkyl group, or a lower alkyl group substituted with a halogen atom), a group represented by the formula —N⁺R⁴R⁵ ·Q⁻ (wherein each of R⁴ and R⁵, which may be the same or different, is a lower alkyl group or a lower alkyl group substituted with a halogen atom, and Q is a halogen atom, a group represented by the formula R⁶COO (wherein R⁶ is a lower alkyl group or a lower alkyl group substituted with a halogen atom) or a group represented by the formula R⁷SO₃ (wherein R⁷ is a lower alkyl group, a lower alkyl group substituted with a halogen atom or a phenyl group which may be substituted with a lower alkyl group);

X¹ and X², which may be the same or different, each is a halogen atom, a group represented by the formula R⁸COO (wherein R⁸ is a lower alkyl group or a lower alkyl group substituted with a halogen atom) or a group represented by the formula R⁹SO₃ (wherein R⁹ a lower alkyl group, a lower alkyl group substituted with a halogen atom or a phenyl group which may be substituted with a lower alkyl group);

X is a halogen atom, or a group represented by the formula R⁹SO₃ (wherein R⁹ is a lower alkyl group, a lower alkyl group substituted with a halogen atom or a phenyl group which may be substituted with a lower alkyl group); and R¹¹ is a lower alkyl group or a lower alkyl group substituted with a halogen atom.

20. A method of producing the compound of claim 1, or a salt, hydrate, solvate or stereoisomer thereof, comprising:

performing the reaction described by reaction formula 7:

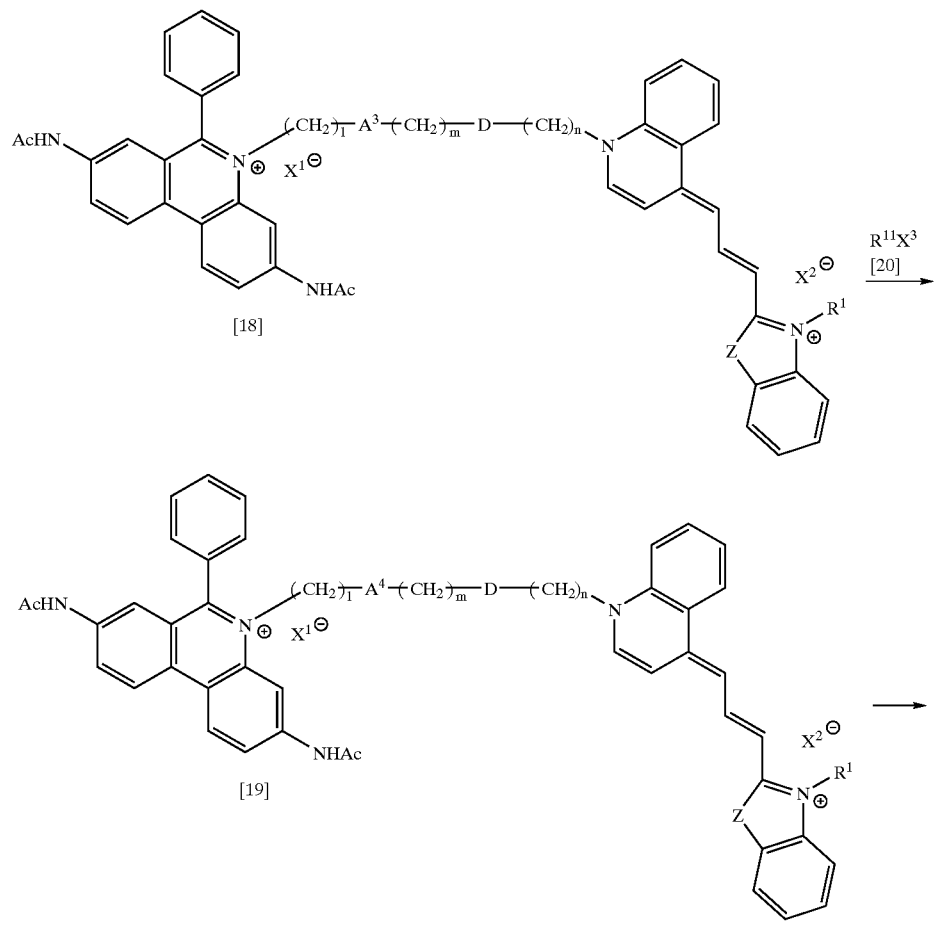

-continued

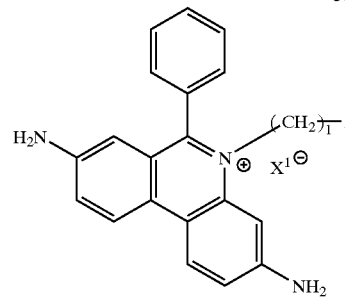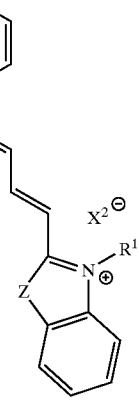

[VII]

wherein
R[1] is a lower alkyl group;
A[3] is a group represented by the formula —NR[3]— (wherein R[3] is a hydrogen atom, a lower alkyl group or a lower alkyl group substituted with a halogen atom);
A[4] is a group represented by —NR[10]— (wherein R[10] is a hydrogen atom, a lower alkyl group, or a lower alkyl group substituted with a halogen atom), a group represented by the formula —N$^+$R[4]R[5]·Q$^-$— (wherein each of R[4] and R[5], which may be the same or different, is a lower alkyl group or a lower alkyl group substituted with a halogen atom, and Q is a halogen atom, a group represented by the formula R[6]COO (wherein R[6] is a lower alkyl group or a lower alkyl group substituted with a halogen atom) or a group represented by the formula R[7]SO$_3$ (wherein R[7] is a lower alkyl group, a lower alkyl group substituted with a halogen atom or a phenyl group which may be substituted with a lower alkyl group));
D is a group represented by the formula —CHR[2]— (wherein R[2] is a hydrogen atom, a lower alkyl group or a lower alkyl group substituted with a halogen atom), a group represented by the formula —NR[3]— (wherein R[3] is a hydrogen atom, a lower alkyl group or a lower alkyl group substituted with a halogen atom), a group represented by the formula —N$^+$R[4]R[5]·Q$^-$— (wherein each of R[4] and R[5], which may be the same or different, is a lower alkyl group or a lower alkyl group substituted with a halogen atom, and Q is a halogen atom, a group represented by the formula R[6]COO (wherein R[6] is a lower alkyl group or a lower alkyl group substituted with a halogen atom) or a group represented by the formula R[7]SO$_3$ (wherein R[7] is a lower alkyl group, a lower alkyl group substituted with a halogen atom or a phenyl group which may be substituted with a lower alkyl group)), an oxygen atom or a sulfur atom;
1, m and n, which may be the same or different, each is an integer of from 2 to 5;
Z is an oxygen atom or a sulfur atom;
X[1] and X[2], which may be the same or different, each is a halogen atom, a group represented by the formula R[8]COO (wherein R[8] is a lower alkyl group or a lower alkyl group substituted with a halogen atom) or a group represented by the formula R[9]SO$_3$ (wherein R[9] is a lower alkyl group, a lower alkyl group substituted with a halogen atom or a phenyl group which may be substituted with a lower alkyl group);
X[3] is a halogen atom, or a group represented by the formula R[9]SO$_3$ (wherein R[9] is a lower alkyl group, a lower alkyl group substituted with a halogen atom or a phenyl group which may be substituted with a lower alkyl group); and
R[11] is a lower alkyl group or a lower alkyl group substituted with a halogen atom.

21. A method of producing the compound of claim 1, or a salt, hydrate, solvate or stereoisomer thereof, comprising:
performing the reaction described by reaction formula 8:

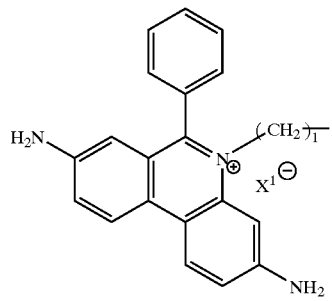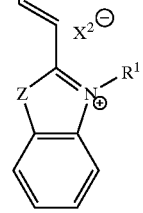

[VI]

-continued

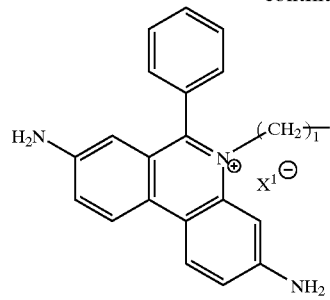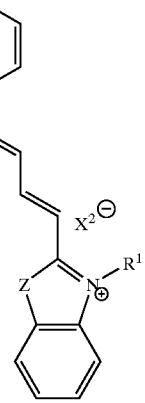

[VII]

wherein
R¹ is a lower alkyl group;
A³ is a group represented by the formula —NR³— (wherein R³ is a hydrogen atom, a lower alkyl group or a lower alkyl group substituted with a halogen atom);
A⁴ is a group represented by —NR¹⁰— (wherein R¹⁰ is a hydrogen atom, a lower alkyl group, or a lower alkyl group substituted with a halogen atom), a group represented by the formula —N⁺R⁴R⁵·Q⁻— (wherein each of R⁴ and R⁵, which may be the same or different, is a lower alkyl group or a lower alkyl group substituted with a halogen atom, and Q is a halogen atom, a group represented by the formula R⁶COO (wherein R⁶ is a lower alkyl group or a lower alkyl group substituted with a halogen atom) or a group represented by the formula R⁷SO₃ (wherein R⁷ is a lower alkyl group, a lower alkyl group substituted with a halogen atom or a phenyl group which may be substituted with a lower alkyl group);
D is a group represented by the formula —CHR²— (wherein R² is a hydrogen atom, a lower alkyl group or a lower alkyl group substituted with a halogen atom), a group represented by the formula —NR³— (wherein R³ is a hydrogen atom, a lower alkyl group or a lower alkyl group substituted with a halogen atom), a group represented by the formula —N⁺R⁴R⁵·Q⁻— (wherein each of R⁴ R⁵, which may be the same or different, is a lower alkyl group or a lower alkyl group substituted with a halogen atom, and Q is a halogen atom, a group represented by the formula R⁶COO (wherein R⁶ is a lower alkyl group or a lower alkyl group substituted with a halogen atom) or a group represented by the formula R⁷SO₃ (wherein R⁷ is a lower alkyl group, a lower alkyl group substituted with a halogen atom or a phenyl group which may be substituted with a lower alkyl group)), an oxygen atom or a sulfur atom;
l, m and n, which may be the same or different, each is an integer of from 2 to 5;
Z is an oxygen atom or a sulfur atom;
X¹ and X², which may be the same or different, each is a halogen atom, a group represented by the formula R⁸COO (wherein R⁸ is a lower alkyl group or a lower alkyl group substituted with a halogen atom) or a group represented by the formula R⁹SO₃ (wherein R⁹ is a lower alkyl group, a lower alkyl group substituted with a halogen atom or a phenyl group which may be substituted with a lower alkyl group);
X³ is a halogen atom, or a group represented by the formula R⁹SO₃ (wherein R⁹ is a lower alkyl group, a lower alkyl group substituted with a halogen atom or a phenyl group which may be substituted with a lower alkyl group); and
R¹¹ is a lower alkyl group or a lower alkyl group substituted with a halogen atom.

* * * * *